(12) United States Patent
Scheib et al.

(10) Patent No.: US 9,044,229 B2
(45) Date of Patent: Jun. 2, 2015

(54) SURGICAL FASTENER INSTRUMENTS

(75) Inventors: Charles J. Scheib, Loveland, OH (US); Jeevan M. Shankarsetty, Bangalore (IN)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1041 days.

(21) Appl. No.: 13/048,559

(22) Filed: Mar. 15, 2011

(65) Prior Publication Data
US 2012/0234899 A1  Sep. 20, 2012

(51) Int. Cl.
| | |
|---|---|
| A61B 17/04 | (2006.01) |
| A61B 17/10 | (2006.01) |
| A61B 17/072 | (2006.01) |
| A61B 17/064 | (2006.01) |
| A61B 17/12 | (2006.01) |
| A61B 17/128 | (2006.01) |
| A61B 17/68 | (2006.01) |
| A61B 17/132 | (2006.01) |
| A61B 17/00 | (2006.01) |

(52) U.S. Cl.
CPC ............ *A61B 17/07207* (2013.01); *A61B 17/68* (2013.01); *A61B 17/0643* (2013.01); *A61B 17/12013* (2013.01); *A61B 17/1285* (2013.01); *A61B 17/1322* (2013.01); *A61B 2017/00004* (2013.01); *A61B 2017/0462* (2013.01)

(58) Field of Classification Search
CPC .................................................... A61B 17/068
USPC ........................................... 227/175.1–182.1
See application file for complete search history.

(56) References Cited

U.S. PATENT DOCUMENTS

| | | | |
|---|---|---|---|
| 4,448,194 A * | 5/1984 | DiGiovanni et al. ......... 606/145 |
| 5,417,700 A | 5/1995 | Egan | |
| 5,702,409 A | 12/1997 | Rayburn et al. | |
| 5,810,855 A | 9/1998 | Rayburn et al. | |
| 5,843,096 A | 12/1998 | Igaki et al. | |
| 5,865,361 A | 2/1999 | Milliman et al. | |
| 6,017,356 A | 1/2000 | Frederick et al. | |
| 6,423,088 B1 | 7/2002 | Fenton, Jr. | |
| 7,000,818 B2 | 2/2006 | Shelton, IV et al. | |
| 7,328,828 B2 | 2/2008 | Ortiz et al. | |
| 7,354,447 B2 | 4/2008 | Shelton, IV et al. | |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

U.S. Appl. No. 13/048,608, filed Mar. 15, 2011.

(Continued)

*Primary Examiner* — Robert Long

(57) ABSTRACT

Surgical instruments and cartridges for cutting and fastening tissues and organs such as vessels are disclosed. In various non-limiting forms, the surgical instrument includes a first jaw that operably supports a substantially flexible elongated tissue closure assembly therein. A second jaw is movably supported relative to the first jaw and is selectively movable between open and closed positions in response to opening and closing motions applied thereto. A closure retraction assembly is configured to selectively apply cinching motions to the substantially flexible elongated tissue closure assembly.

23 Claims, 18 Drawing Sheets

(56) References Cited

U.S. PATENT DOCUMENTS

| | | | |
|---|---|---|---|
| 7,407,078 B2 | 8/2008 | Shelton, IV et al. |
| 7,416,101 B2 | 8/2008 | Shelton, IV et al. |
| 7,422,139 B2 | 9/2008 | Shelton, IV et al. |
| 7,431,189 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,490,749 B2 | 2/2009 | Schall et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,549,564 B2 | 6/2009 | Boudreaux |
| 7,568,603 B2 | 8/2009 | Shelton, IV et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,641,095 B2 * | 1/2010 | Viola ................. 227/176.1 |
| 7,644,848 B2 | 1/2010 | Swayze et al. |
| 7,651,017 B2 * | 1/2010 | Ortiz et al. ............ 227/176.1 |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,731,072 B2 | 6/2010 | Timm et al. |
| 7,735,703 B2 | 6/2010 | Morgan et al. |
| 7,736,374 B2 * | 6/2010 | Vaughan et al. ............. 606/153 |
| 7,738,971 B2 | 6/2010 | Swayze et al. |
| 7,740,159 B2 | 6/2010 | Shelton, IV et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,934,630 B2 | 5/2011 | Shelton, IV et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,966,799 B2 | 6/2011 | Morgan et al. |
| 7,980,443 B2 | 7/2011 | Scheib et al. |
| 7,992,757 B2 | 8/2011 | Wheeler et al. |
| 8,011,550 B2 | 9/2011 | Aranyi et al. |
| 8,011,555 B2 | 9/2011 | Tarinelli et al. |
| 8,020,743 B2 | 9/2011 | Shelton, IV |
| 8,056,787 B2 | 11/2011 | Boudreaux et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 8,231,043 B2 | 7/2012 | Tarinelli et al. |
| 8,353,438 B2 | 1/2013 | Baxter, III et al. |
| 8,540,131 B2 | 9/2013 | Swayze |
| 2005/0267325 A1 * | 12/2005 | Bouchier et al. ................. 600/37 |
| 2006/0011699 A1 | 1/2006 | Olson et al. |
| 2007/0102472 A1 | 5/2007 | Shelton, IV |
| 2007/0106317 A1 | 5/2007 | Shelton, IV et al. |
| 2007/0114261 A1 * | 5/2007 | Ortiz et al. ................. 227/175.1 |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0225562 A1 | 9/2007 | Spivey et al. |
| 2007/0239028 A1 | 10/2007 | Houser et al. |
| 2007/0282356 A1 * | 12/2007 | Sonnenschein et al. ...... 606/153 |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082125 A1 | 4/2008 | Murray et al. |
| 2008/0082126 A1 | 4/2008 | Murray et al. |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0208324 A1 | 8/2008 | Glithero et al. |
| 2008/0287988 A1 * | 11/2008 | Smith et al. ................... 606/216 |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0149871 A9 | 6/2009 | Kagan et al. |
| 2009/0188964 A1 * | 7/2009 | Orlov ........................ 227/175.3 |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |

(56) References Cited

U.S. PATENT DOCUMENTS

| | | |
|---|---|---|
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209990 A1 | 8/2009 | Yates et al. |
| 2009/0242610 A1 | 10/2009 | Shelton, IV et al. |
| 2010/0012704 A1 | 1/2010 | Tarinelli Racenet et al. |
| 2010/0032470 A1 | 2/2010 | Hess et al. |
| 2010/0069942 A1 | 3/2010 | Shelton, IV |
| 2010/0072254 A1 | 3/2010 | Aranyi et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0147922 A1* | 6/2010 | Olson .................. 227/176.1 |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2010/0320252 A1* | 12/2010 | Viola et al. .................. 227/176.1 |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0087279 A1* | 4/2011 | Shah et al. ............... 606/219 |
| 2011/0095070 A1* | 4/2011 | Patel et al. .............. 227/181.1 |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174861 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0226837 A1 | 9/2011 | Baxter, III et al. |
| 2011/0233258 A1 | 9/2011 | Boudreaux |
| 2011/0253766 A1 | 10/2011 | Baxter, III et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0061448 A1 | 3/2012 | Zingman |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080334 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175398 A1* | 7/2012 | Sandborn et al. .......... 227/175.1 |
| 2012/0175399 A1 | 7/2012 | Shelton et al. |
| 2012/0199630 A1 | 8/2012 | Shelton, IV et al. |
| 2012/0199631 A1 | 8/2012 | Shelton, IV et al. |

(56) References Cited

U.S. PATENT DOCUMENTS

| | | |
|---|---|---|
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239012 A1 | 9/2012 | Laurent et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, Iv et al. |
| 2012/0283707 A1 | 11/2012 | Giordano et al. |
| 2012/0283748 A1 | 11/2012 | Ortiz et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2013/0012931 A1 | 1/2013 | Spivey et al. |
| 2013/0012957 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0062391 A1* | 3/2013 | Boudreaux et al. ........ 227/175.1 |
| 2013/0075443 A1 | 3/2013 | Giordano et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0105551 A1 | 5/2013 | Zingman |
| 2013/0126581 A1 | 5/2013 | Yates et al. |
| 2013/0126582 A1 | 5/2013 | Shelton, IV et al. |
| 2013/0126583 A1 | 5/2013 | Hueil et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |
| 2013/0233908 A1* | 9/2013 | Knodel et al. ............ 227/177.1 |

FOREIGN PATENT DOCUMENTS

| | | |
|---|---|---|
| CA | 2514274 A1 | 1/2006 |
| CN | 2488482 Y | 5/2002 |
| CN | 1523725 A | 8/2004 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| CN | 101023879 B | 3/2013 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 4228909 A1 | 3/1994 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |

(56) References Cited

FOREIGN PATENT DOCUMENTS

| | | |
|---|---|---|
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1487359 B1 | 10/2007 |
| EP | 1599146 81 | 10/2007 |
| EP | 1839596 A1 | 10/2007 |
| EP | 2110083 A2 | 10/2007 |
| EP | 1857057 A2 | 11/2007 |
| EP | 1402821 B1 | 12/2007 |
| EP | 1872727 A1 | 1/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1330201 B1 | 6/2008 |
| EP | 1702568 B1 | 7/2008 |
| EP | 1943955 A2 | 7/2008 |
| EP | 1943957 A2 | 7/2008 |

(56) References Cited

FOREIGN PATENT DOCUMENTS

| | | |
|---|---|---|
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000102 A2 | 12/2008 |
| EP | 2005894 A2 | 12/2008 |
| EP | 2008595 A2 | 12/2008 |
| EP | 1736104 B1 | 3/2009 |
| EP | 1749486 B1 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550409 A1 | 6/2009 |
| EP | 1550413 B1 | 6/2009 |
| EP | 1745748 B1 | 8/2009 |
| EP | 2090237 A1 | 8/2009 |
| EP | 2090241 A1 | 8/2009 |
| EP | 2090245 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 1607050 B1 | 12/2009 |
| EP | 1815804 B1 | 12/2009 |
| EP | 2165660 A2 | 3/2010 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1647286 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 1627605 B1 | 12/2010 |
| EP | 1994890 B1 | 1/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 1813205 B1 | 6/2011 |
| EP | 2090243 B1 | 6/2011 |
| EP | 2329773 A1 | 6/2011 |
| EP | 1908414 B1 | 11/2011 |
| EP | 2153781 B1 | 11/2011 |
| EP | 1847225 B1 | 12/2011 |
| EP | 1785102 B1 | 1/2012 |
| EP | 2090253 B1 | 3/2012 |
| EP | 2005895 B1 | 8/2012 |
| EP | 2090248 B1 | 8/2012 |
| EP | 1884206 B1 | 3/2013 |
| EP | 2090244 B1 | 10/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | 50-33988 U | 4/1975 |
| JP | S 58500053 A | 1/1983 |
| JP | 61-98249 A | 5/1986 |
| JP | S 61502036 A | 9/1986 |
| JP | S 63-59764 A | 3/1988 |
| JP | S 63-147449 A | 6/1988 |
| JP | 63-203149 | 8/1988 |
| JP | H 02-279149 A | 11/1990 |
| JP | 3-12126 A | 1/1991 |
| JP | 5-212039 A | 8/1993 |
| JP | 6007357 A | 1/1994 |
| JP | H 6-30945 A | 2/1994 |
| JP | H 06-26812 U | 4/1994 |
| JP | H 6-121798 A | 5/1994 |
| JP | 7051273 A | 2/1995 |
| JP | 7-124166 A | 5/1995 |
| JP | 7-255735 A | 10/1995 |
| JP | 8-33642 A | 2/1996 |
| JP | 8033641 A | 2/1996 |
| JP | 8-164141 A | 6/1996 |
| JP | 8229050 A | 9/1996 |
| JP | H 09-501081 A | 2/1997 |
| JP | 10-512469 | 12/1998 |
| JP | 2000-14632 | 1/2000 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001-517473 A | 10/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-164066 | 6/2003 |
| JP | 2003-521301 A | 7/2003 |
| JP | 2004-162035 A | 6/2004 |
| JP | 2004-531280 A | 10/2004 |
| JP | 2004-532084 A | 10/2004 |
| JP | 2004-329624 A | 11/2004 |
| JP | 2004-344663 | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005505322 T | 2/2005 |
| JP | 2005-103280 A | 4/2005 |
| JP | 2005-511131 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-144183 A | 6/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-034975 A | 2/2006 |
| JP | 2006-034980 A | 2/2006 |
| JP | 2006-506106 A | 2/2006 |
| JP | 2006-218297 A | 8/2006 |
| JP | 2006-281405 A | 10/2006 |
| JP | 2007-098130 A | 4/2007 |
| JP | 3906843 B2 | 4/2007 |
| JP | 2007-117725 A | 5/2007 |
| JP | 2007-203051 A | 8/2007 |
| JP | 2007-203057 A | 8/2007 |
| JP | 2007-229448 A | 9/2007 |
| JP | 2007-325922 A | 12/2007 |
| JP | 2008-283459 A | 11/2008 |
| JP | 2009-506799 A | 2/2009 |
| JP | 2010-098844 A | 4/2010 |
| RU | 2008830 C1 | 3/1994 |

(56) References Cited

FOREIGN PATENT DOCUMENTS

| | | |
|---|---|---|
| RU | 2141279 C1 | 11/1999 |
| RU | 2187249 C2 | 8/2002 |
| RU | 2225170 C2 | 3/2004 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/17737 | 8/1994 |
| WO | WO 94/18893 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A2 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |

(56) References Cited

FOREIGN PATENT DOCUMENTS

| | | |
|---|---|---|
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/058079 A2 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/109125 A1 | 9/2008 |
| WO | WO 2008/124748 A1 | 10/2008 |
| WO | WO 2009/023851 A1 | 2/2009 |
| WO | WO 2009/046394 A1 | 4/2009 |
| WO | WO 2009/137761 A2 | 11/2009 |
| WO | WO 2009/143092 A1 | 11/2009 |
| WO | WO 2010/030434 A1 | 3/2010 |
| WO | WO 2010/054404 A1 | 5/2010 |
| WO | WO 2010/063795 A1 | 6/2010 |
| WO | WO 2010/098871 A2 | 9/2010 |
| WO | WO 2012/021671 A1 | 2/2012 |
| WO | WO 2012/044844 A2 | 4/2012 |

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print. cfm?ArticleID=17465, accessed Jan. 15, 2008 (5 pages).

Datasheet for Panasonic TK Relays Ultra Low Profile 2 a Polarized Relay, Copyright Matsushita Electric Works, Ltd. (Known of at least as early as Aug. 17, 2010), 5 pages.

International Search Report for PCT/US2012/028899, dated Jul. 26, 2012 (4 pages).

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

(56) References Cited

OTHER PUBLICATIONS

Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 30-112.
Hoffman, "Hydrogels for Biomedical Applications," Advanced Drug Delivery Reviews, 54 (2002) pp. 30-112.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.

* cited by examiner

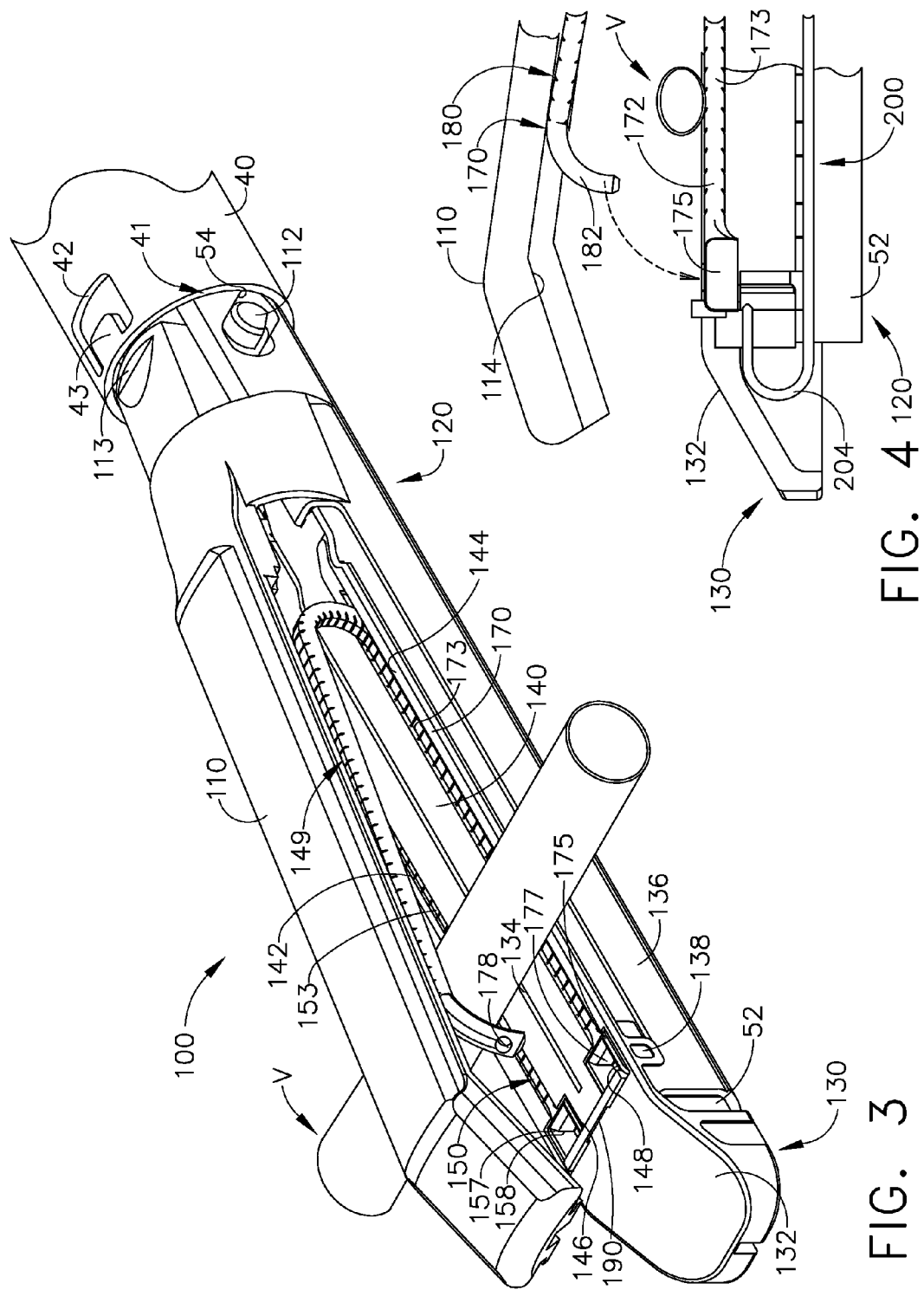

FIG. 19

SURGICAL FASTENER INSTRUMENTS

BACKGROUND

1. Technical Field

The present invention relates to surgical instruments and, in various embodiments, to surgical cutting and fastening instruments for cutting and fastening tissue and organs such as vessels and the like.

2. Background

Surgical staplers have been used to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil that has staple-forming pockets aligned with rows of unformed staples supported in the cartridge. Examples of such devices are disclosed in U.S. Pat. No. 7,000,818, entitled "Surgical Stapling Instrument Having Separate Distinct Closing and Firing Systems", issued Feb. 21, 2006, the disclosure of which is herein incorporated by reference in its entirety. Other surgical cutting and stapling instruments employ what is commonly referred to as a "disposable loading unit" or "DLU". Such devices support a staple cartridge and a fresh knife in the form of a "unit" that is configured to be operably attached to the surgical stapling instrument. The units are designed to be discarded after the staples have been fired. Examples of such instruments are disclosed in U.S. Pat. No. 5,865,361 entitled "Surgical Stapling Apparatus", issued Feb. 2, 1999, the entire disclosure of which is herein incorporated by reference.

In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

Current methods of vascular transection employ one of the above-described endocutter devices to apply staples to achieve hemostasis. However, the staples punch through the vessel during their formation which thereby increases the possibility of a leak and also prolongs the healing time. Such leaks which emanate from the transection site can at times be difficult to locate.

Accordingly, there is a need for surgical staple cartridge arrangements that address many of the challenges discussed above.

The foregoing discussion is intended only to illustrate some of the shortcomings present in the field of the invention at the time, and should not be taken as a disavowal of claim scope.

SUMMARY

In accordance with general aspects of at least one form, there is provided a surgical fastening instrument that includes a first jaw that operably supports a substantially flexible elongated tissue closure assembly therein. A second jaw is movably supported relative to the first jaw and is selectively movable between open and closed positions in response to opening and closing motions applied thereto. A closure retraction assembly is configured to selectively apply cinching motions to the substantially flexible elongated tissue closure assembly.

In accordance with other general aspects of at least one form, there is provided a fastener cartridge for cutting and occluding a vessel. In at least one form, the fastener cartridge comprises a body portion that has a deck face and a centrally disposed slot therein for receiving a cutting member of a surgical instrument therethrough. The deck face is configured to operably support a pair of substantially flexible elongated closure members wherein one member is supported on a first side of the centrally disposed slot and the other member is disposed on a second side of the slot. A closure retraction assembly is at least partially operably supported in the body portion and is configured to selectively apply cinching motions to each of the substantially flexible elongated closure members.

In accordance with still other general aspects of at least one form, there is provided a closure assembly for use with a surgical fastener cartridge that has a closure retraction assembly therein. In at least one form, the closure assembly comprises a first absorbable closure member that has a first lower elongated portion that is supportable on a portion of the fastener cartridge. The first absorbable closure member has a first locking end that defines a first locking aperture. The first absorbable closure member further has a first upper elongated portion that is integrally formed with the first lower elongated portion. The first closure member further has a first hook-shaped end that is supported in spaced relation to the first locking end. The closure assembly further includes a second absorbable closure member that has a second lower elongated portion that is supportable on another portion of the fastener cartridge and has a second locking end that defines a second locking aperture. The second absorbable closure member has a second upper elongated portion that is integrally formed with the second lower elongated portion and has a second hook-shaped end that is supported in spaced relation to the first locking end. A bridge member couples the first absorbable closure member and the second absorbable closure member in spaced relation to each other.

BRIEF DESCRIPTION OF DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 3 is a perspective view one form of a non-limiting end effector embodiment supporting a portion of a vessel therein;

FIG. 4 is a cross-sectional view of a portion of the end effector of FIG. 3;

FIG. 19 is a perspective view of one form of another non-limiting end effector embodiment.

DETAILED DESCRIPTION

Figure 1:
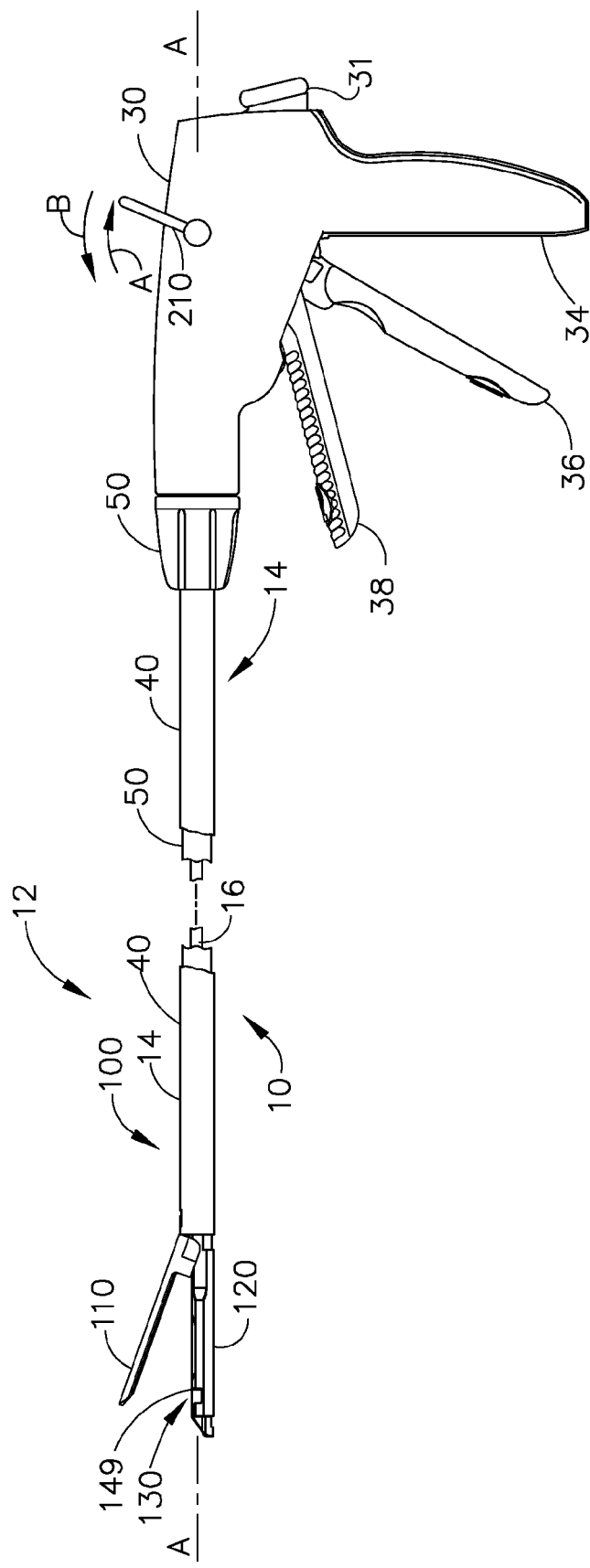
FIG. 1 is a side view of one form of a non-limiting surgical cutting and fastening instrument embodiment.

The Applicant of the present application also owns U.S. Patent Application entitled "Surgical Staple Cartridges With Tissue Tethers For Manipulating Divided Tissues and Methods of Using Same", Ser. No. 13/048,608, now U.S. Pat. No. 8,540,131, which was filed on even date herewith and which is herein incorporated by reference in its entirety.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with "open" surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device such as a trocar that has a working channel through which the end effector and elongated shaft of a surgical instrument can be advanced.

Turning to the Drawings wherein like numerals denote like components throughout the several views, FIG. 1 depicts one embodiment of a surgical instrument 10 that is capable of practicing various unique benefits of at least one form of the present invention. As shown in FIG. 1, in one non-limiting form, the surgical instrument 10 generally includes a handle portion 30 that is connected to an implement portion 12, the latter further comprising a shaft assembly 14 distally terminating in an end effector 100. The shaft assembly 14 includes a movable closure tube assembly 40 that is axially movable on a spine 50 that extends from the handle portion 30 to be coupled to the end effector 100. As shown in FIG. 1, the shaft assembly 14 does not include an articulation joint for facilitating articulation of the end effector relative to a longitudinal axis A-A defined by the shaft assembly 14. In other non-limiting embodiments, the shaft assembly 14 may include at least one articulation joint for facilitating the articulation of the end effector relative to the longitudinal axis. In this and other non-limiting embodiments, the shaft assembly 14 may operably interface with the handle portion 30 such that the end effector 100 may be selectively rotated about the longitudinal axis A-A. As the present Detailed Description proceeds, it will become apparent that the unique and novel features of various non-limiting embodiments of the present invention may be effectively employed with a variety of different surgical instruments that employ different handle and shaft arrangements. For example, various portions of the instrument 10 may be identical to portions of the surgical instruments disclosed in U.S. Pat. No. 7,000,818, entitled "Surgical Stapling Instrument Having Separate Distinct Closing and Firing Systems", the disclosure of which is herein incorporated by reference in its entirety. Thus, the construction and operation of the components of instrument 10 that are not needed to understand the various embodiments and forms of the present invention will not be specifically discussed herein.

Figure 2:
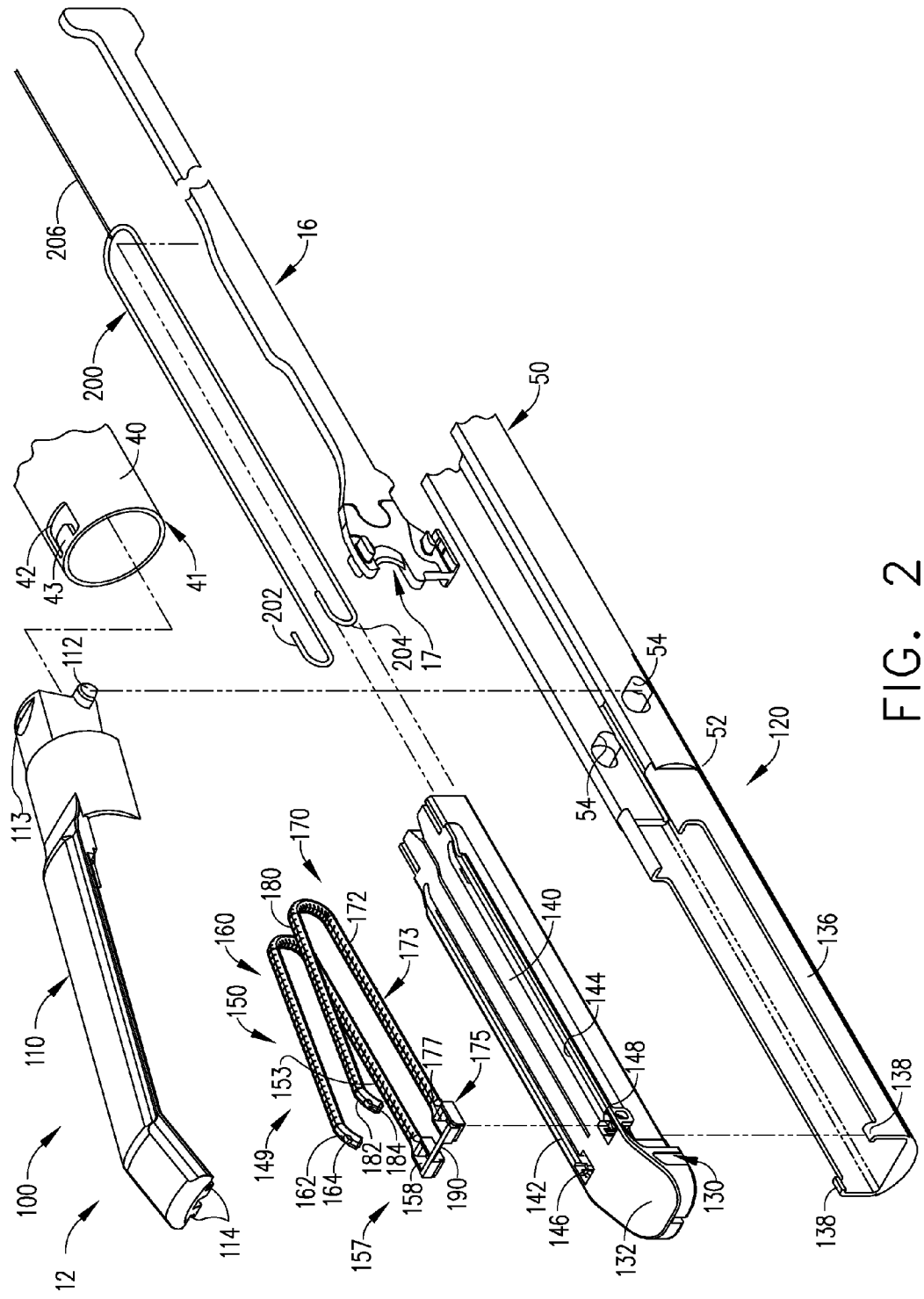
FIG. 2 is a partial exploded assembly view of a non-limiting end effector embodiment.

In at least one non-limiting embodiment, the end effector 100, in general, comprises a pair of "jaws" 110, 120 that are configured to cut and fasten the ends of the severed tissue such as, for example, a vessel. However, while the various non-limiting embodiments disclosed herein are particularly well adapted for cutting and occluding vessels, the various embodiments of the present invention could conceivably be effectively employed to cut and fasten other forms of tissue. As will be discussed in further detail below, jaw 120 supports a tissue fastening cartridge 130 that operably supports a tissue closure assembly 149. See FIG. 2. The instrument 10 includes a firing bar 16 which generally has a sharpened tissue-cutting edge or blade member 17 on a distal portion thereof. As the firing bar 16 is driven distally through the shaft assembly 14 and distally through the vessel fastening cartridge, the tissue-cutting edge severs the tissue clamped between the jaws 110, 120.

In the non-limiting embodiment depicted in FIG. 1, the handle portion 30 is fashioned with a pistol grip 34. A closure trigger 36 is pivotally mounted to the handle portion 30 and operably interfaces with the closure tube assembly 40 to effectuate axial movement thereof on the spine member 50. As the closure trigger 36 is pivotally drawn by the clinician towards the pistol grip portion 34, the closure tube assembly 40 is driven in the distal direction to interact with jaw 120 to cause clamping or closing thereof toward the tissue fastening cartridge 130. The handle portion 30 further supports a firing trigger 38 that is outboard of the closure trigger 36. The firing trigger 38 operably interfaces with the firing bar 16. The firing bar 16 is driven distally when the closure trigger 36 and is pivotally drawn by the clinician towards the pistol grip 34. As the firing bar 16 is driven distally through the tissue fastening cartridge 130, the clamped tissue is severed.

As can be seen in FIGS. 4, 7, 10, and 11, in various non-limiting embodiments, the tissue fastening cartridge 130 is supported on a distal end portion 52 of the spine 50 or it may be supported in an elongated channel that is coupled to the spine 50. The tissue fastening cartridge 130 comprises a cartridge body 132 that may be molded from, for example, a polymer material and be provided with a centrally disposed slot 134 that is configured to operably receive the distal end 17 of the firing bar 16 therein as the firing bar 16 is driven therethrough. The cartridge body 132 may be affixed to the distal end 52 of the spine 50 by a U-shaped cartridge tray 136 that extends around the distal end 52 of the spine 50 and retainingly interfaces with the cartridge body 132. For example, the cartridge body 132 may snappingly interface with snap detents 138 on the cartridge tray 136.

Figure 5:
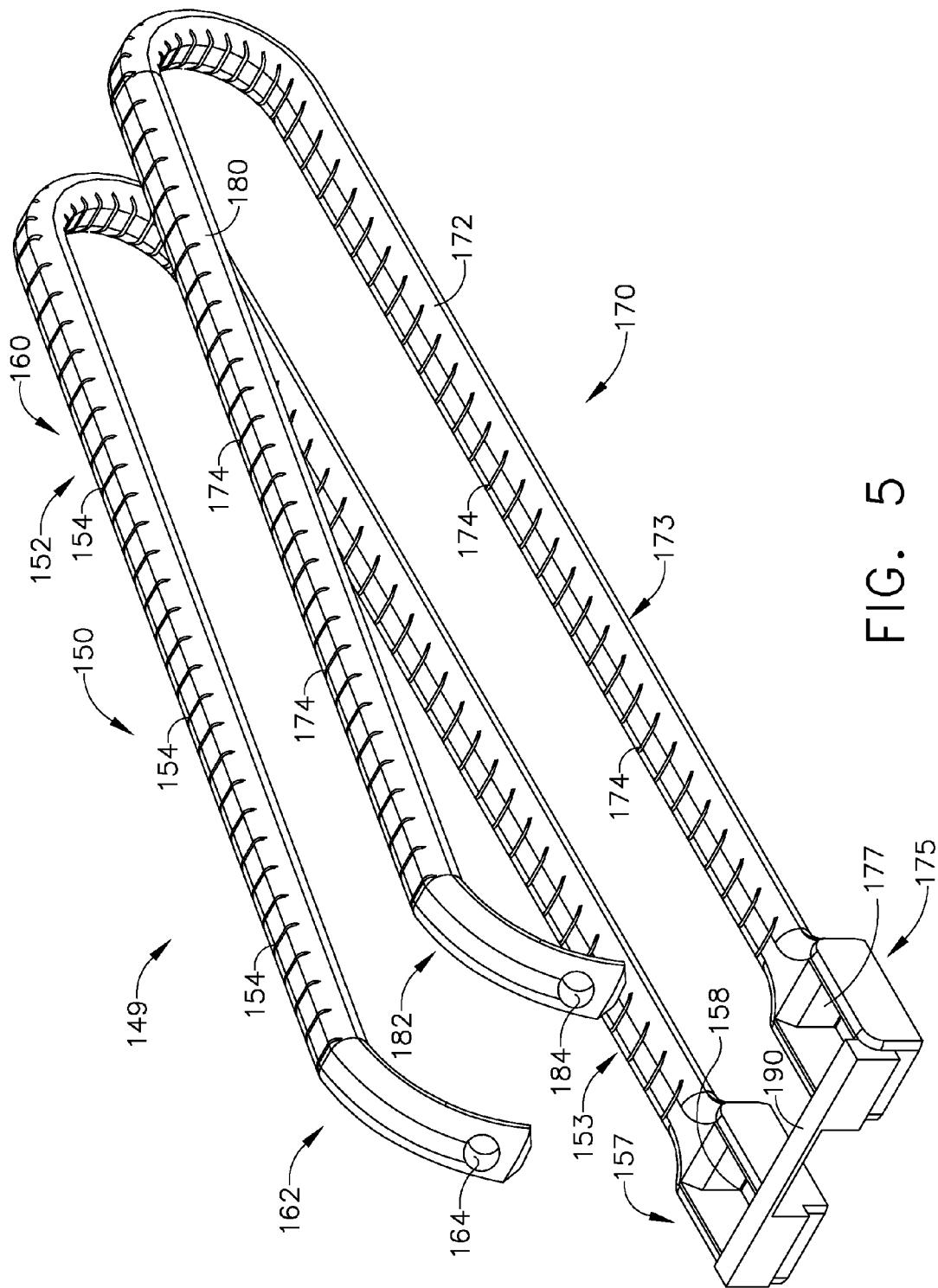
FIG. 5 is a perspective view of one form of a non-limiting closure assembly embodiment.

In various non-limiting embodiments, the tissue fastening cartridge 130 is configured to operably support a flexible elongated tissue closure assembly, generally designated as 149. As can be seen in FIG. 5, in at least one form, the tissue closure assembly 149 includes a pair of interlinked suture strips 150 and 170. The flexible elongated tissue closure assembly 149 includes a first suture strip 150 that has an elongated first body portion 152 that is substantially U-shaped. The first suture strip 150 may be fabricated from a bioabsorbable material and include a first elongated lower portion 153 that terminates in a first lock end 157. The first suture strip 150 further has a first upper portion 160 that terminates in a first hook end 162. Each of the first lower and upper portions 153, 160 has a plurality of slits 154 therein that facilitates the bending and cinching of the suture strip 150 as will be discussed in further detail below. The first lock end 157 defines a first locking cavity, or aperture, 158 that is configured to receive the first hook end 162 therethrough.

The tissue closure assembly 149 further includes a second suture strip 170 that has a second elongated body portion 172 that is substantially U-shaped. The second suture strip 170 may also be fabricated from a bioabsorbable material and include a second elongated lower portion 173 that terminates in a second lock end 175. The second suture strip 170 further has a second upper portion 180 that terminates in a second hook end 182. Each of the second lower and upper portions 173, 180 has a plurality of slits 174 therein that facilitate the bending and cinching of the second suture strip 170 as will be discussed in further detail below. The second lock end 175 defines a second locking cavity, or aperture, 177 that is configured to receive the second hook end 182 therethrough. The second suture strip 170 may be linked to the first suture strip 150 with a bridge member 190 that links the lock ends 157, 175 together.

Figure 5A:
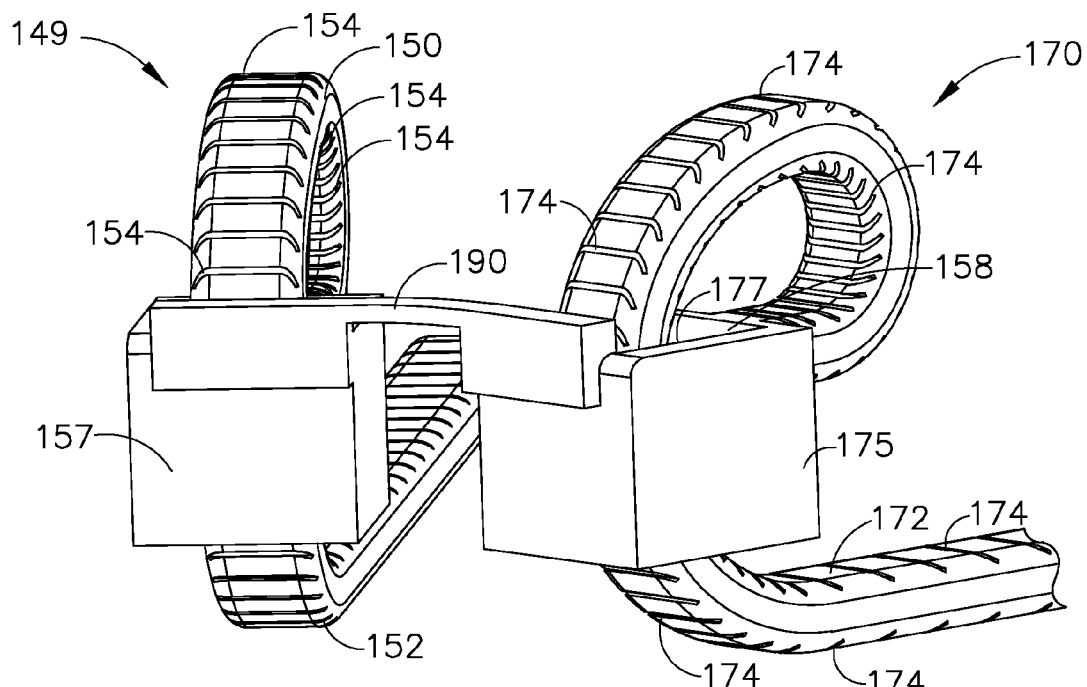
FIG. 5A is a perspective view of the closure assembly of FIG. 5 in a clinched position.
Figure 5B:
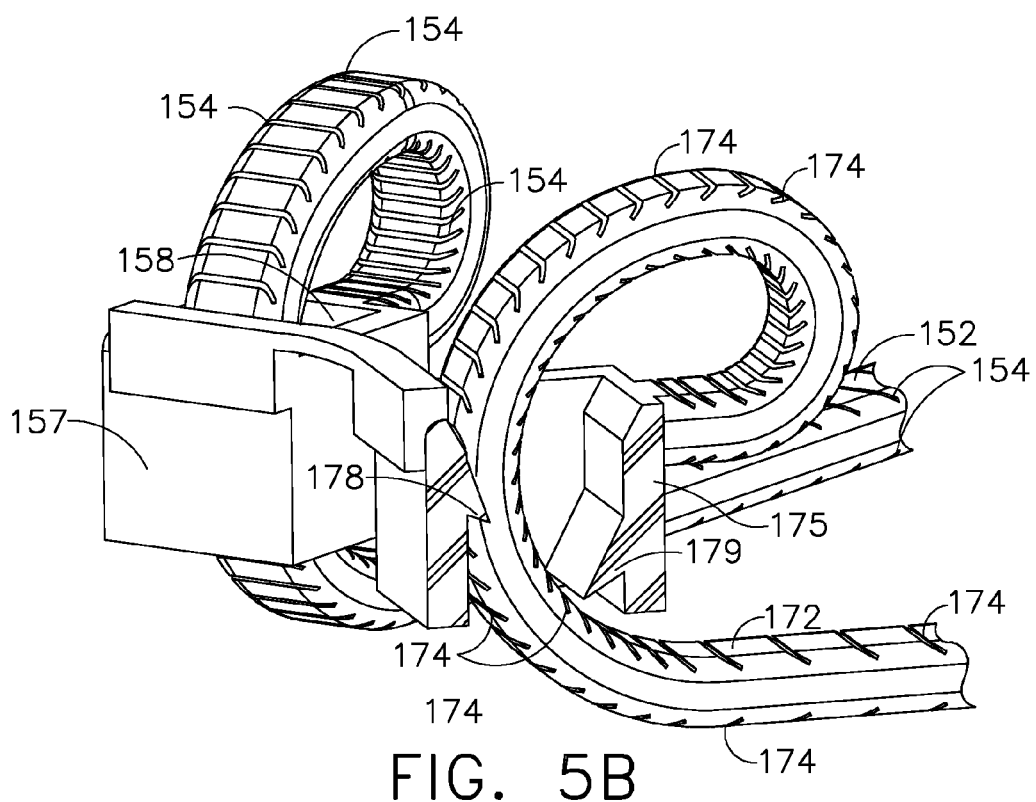
FIG. 5B is another perspective view of the closure assembly of FIGS. 4 and 5A with a lock end thereof shown in cross-section to illustrate the pointed locking tabs in locking engagement with the suture slits to retain the suture in a cinched position.
Figures 6, 7:
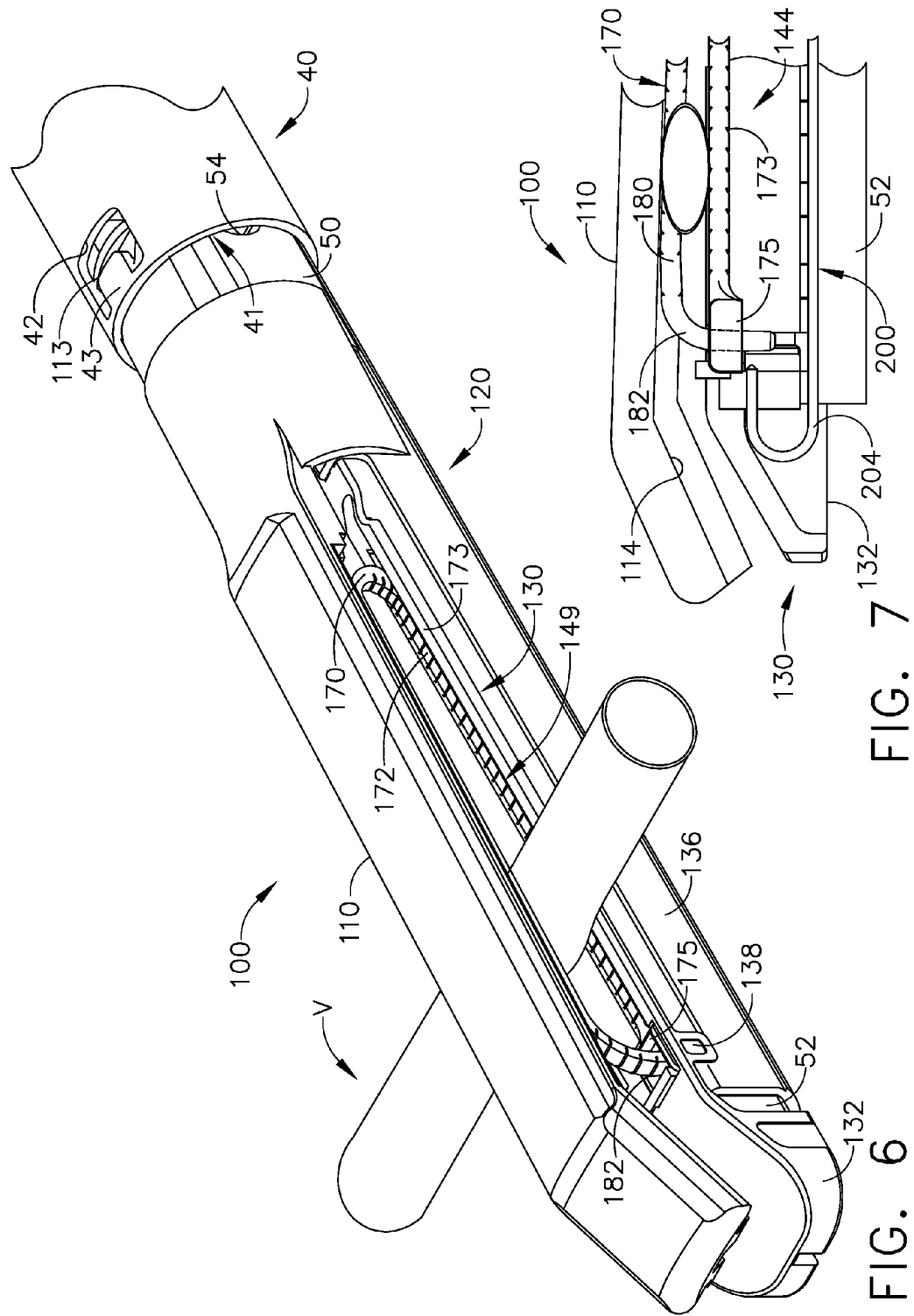
FIG. 6 is another perspective view of the end effector embodiment of FIG. 3 in a partially closed orientation.
FIG. 7 is a cross-sectional view of a portion of the end effector of FIG. 6.
Figure 8:
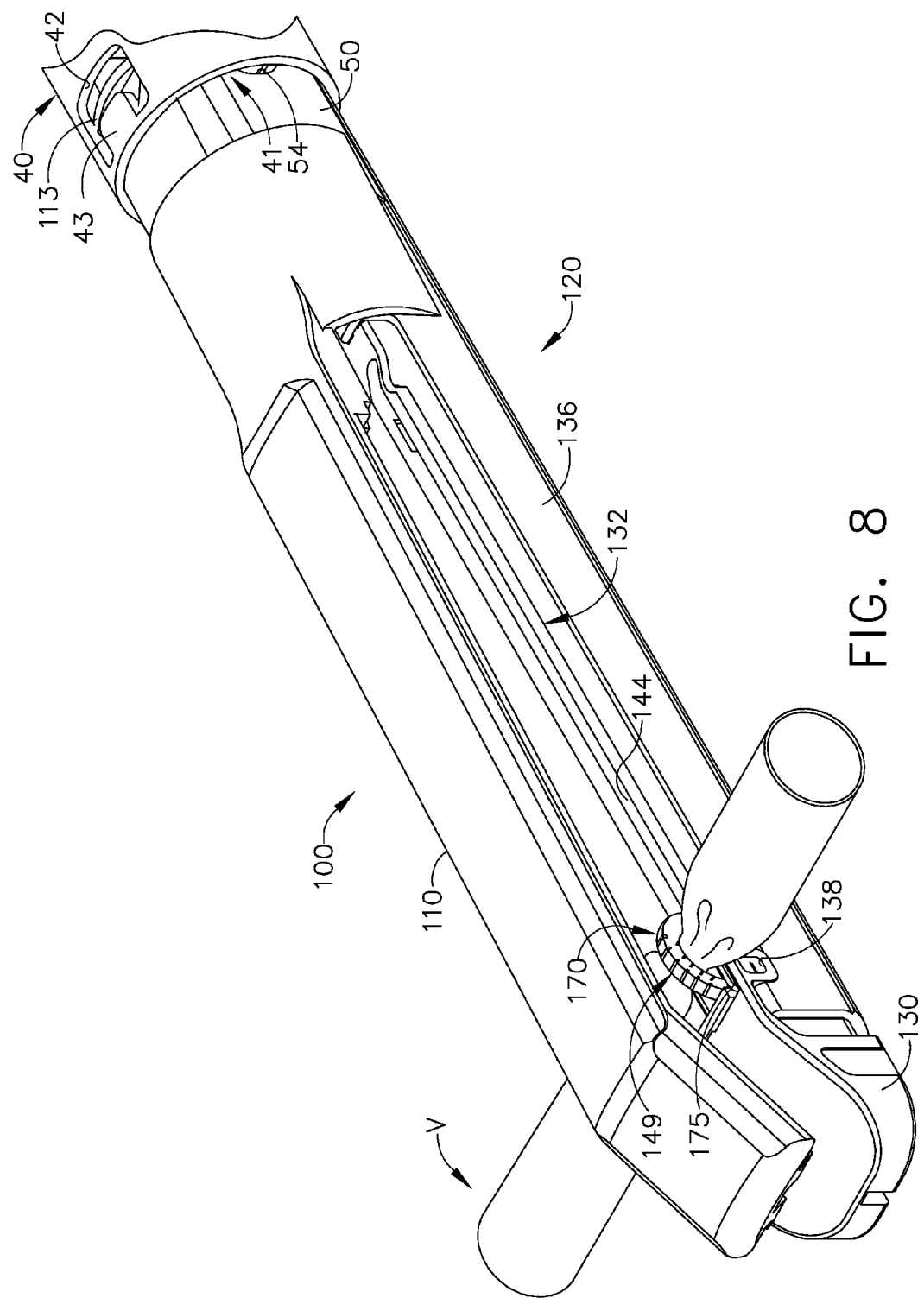
FIG. 8 is another perspective view of the end effector of FIGS. 3 and 6 in a clamped orientation and after the sutures have been cinched around portions of the vessel clamped therein.

FIGS. 5A and 5B further illustrate the tissue closure assembly 149 with each of the suture strips 150, 170 in a cinched orientation. As indicated above, the first suture strip 150 has a plurality of slits 154 therein and the second suture strip 170 has a plurality of slits 174 formed therein. When working on thin walled vessels such as pulmonary veins which are very delicate, any projections on the strips 150, 170 may inadvertently puncture the vessel or otherwise cause trauma. As can be most particularly seen in FIG. 5B, for example, the slits 174 (and likewise, slits 154) are provided at an angle so that when the sutures 150, 170 are cinched, they form a relatively smooth inner surface for compressing the vessel. As can also be seen in FIG. 5B, the lock end 175 may be formed with at least one and preferably a pair of offset pointed locking tabs 178, 179 that are configured to engage the slits 174 on opposing sides of the suture 170 during the cinching process to lock the suture 170 in position. It will be understood that the first lock end 150 is formed with similar pointed locking tabs (not shown).

The cartridge body 132 has a deck face 140 that is in confronting relationship with the underside of jaw 110. The deck face 140 has a first closure-receiving groove 142 for supporting the first lower suture portion 153 and a second closure-receiving groove 144 for supporting the second lower suture portion 173. See FIG. 2. In addition, a first locking receptacle 146 is provided in the cartridge body 132 for receiving the first lock end 157 therein and a second locking receptacle 148 is provided for receiving the second lock end 175 therein as shown.

In various non-limiting embodiments, jaw 110 is selectively movable relative to jaw 120 to clamp a vessel "V" or other tissue therebetween. Jaw 110 is pivotally coupled to the spine 50 by a pair of trunions 112 that extend through elongated trunion slots 54 formed in the spine 50, allowing the jaw 110 to pivot from an open position to a closed position relative to jaw 120 in response to opening and closing motions received from the closure tube assembly 40. As can be seen in FIGS. 2, 3, 6, and 8-11, the distal end 41 of the closure tube assembly 40 includes a horseshoe aperture 42 and tab 43 for engaging an opening tab 113 on jaw 110. When the closure tube assembly 40 is advanced distally on the end effector frame 50, the horseshoe aperture 42 applies a closing motion to the tab 113 to move the jaw 110 toward jaw 120. When the closure tube assembly 40 is withdrawn in the proximal direction, the tab 43 engages the tab 113 to move jaw 110 away from jaw 120 to an open position. In various embodiments, the jaw 110 further has a pair of closure-retaining slots 114 therein for supporting the first upper suture portion 160 and the second upper suture portion 180 therein.

Figure 9:
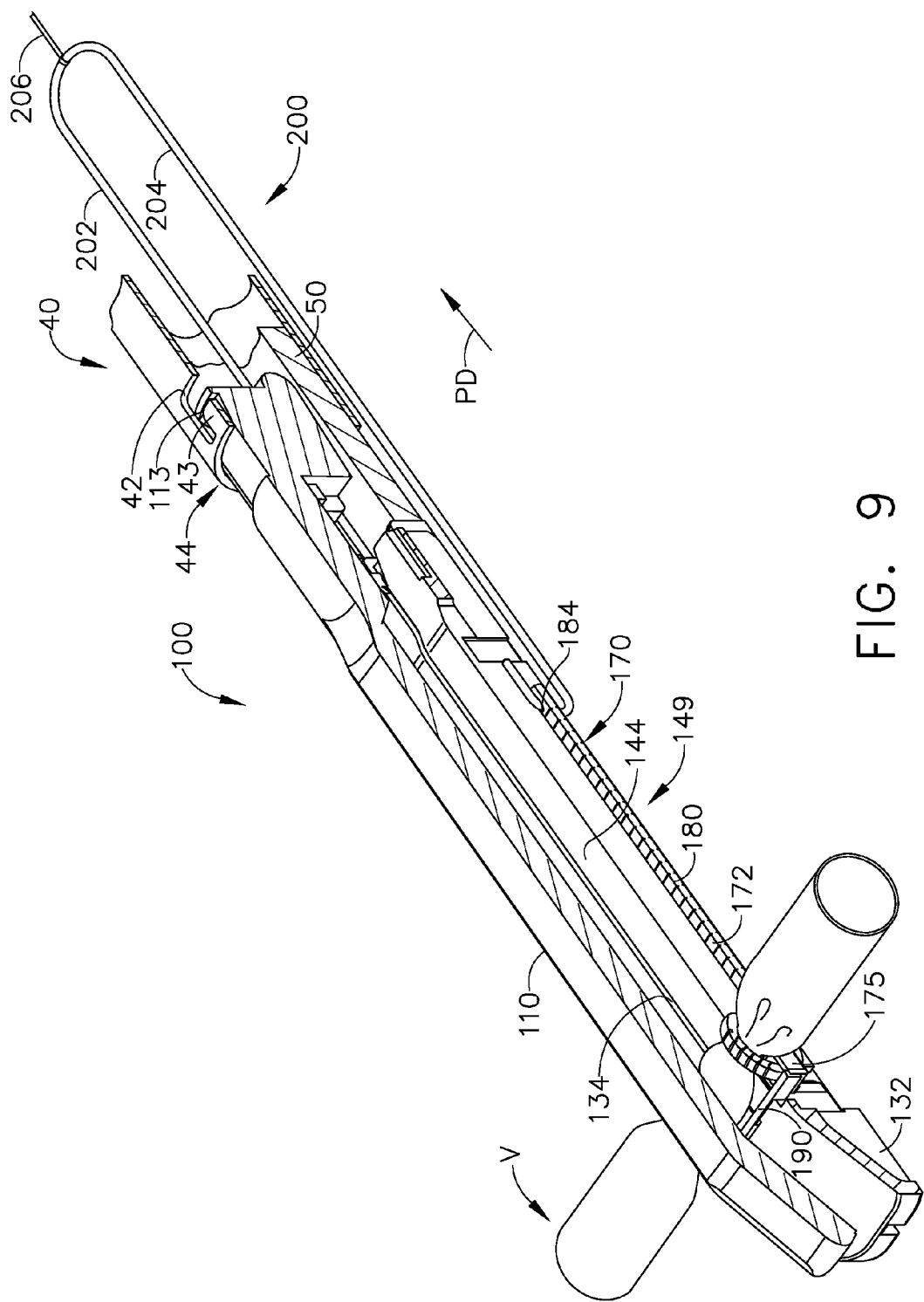
FIG. 9 is a cross-sectional perspective view of the end effector depicted in FIG. 8.
Figure 10:
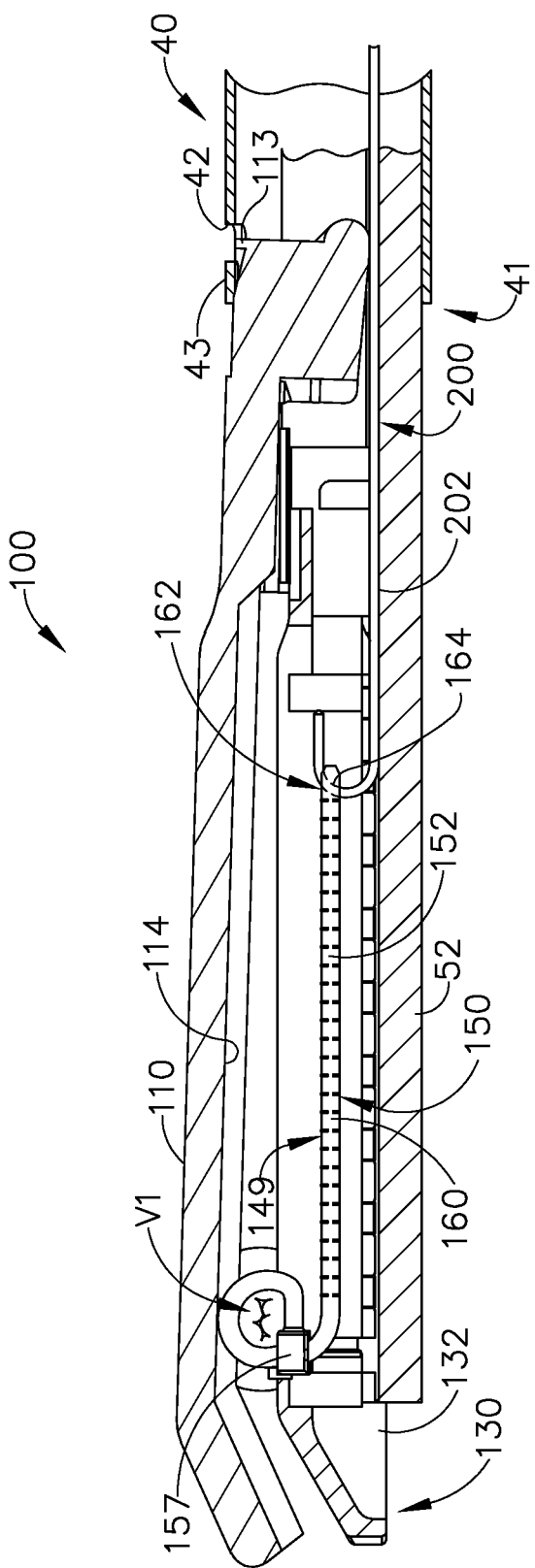
FIG. 10 is another cross-sectional view of the end effector depicted in FIG. 8.
Figure 11:
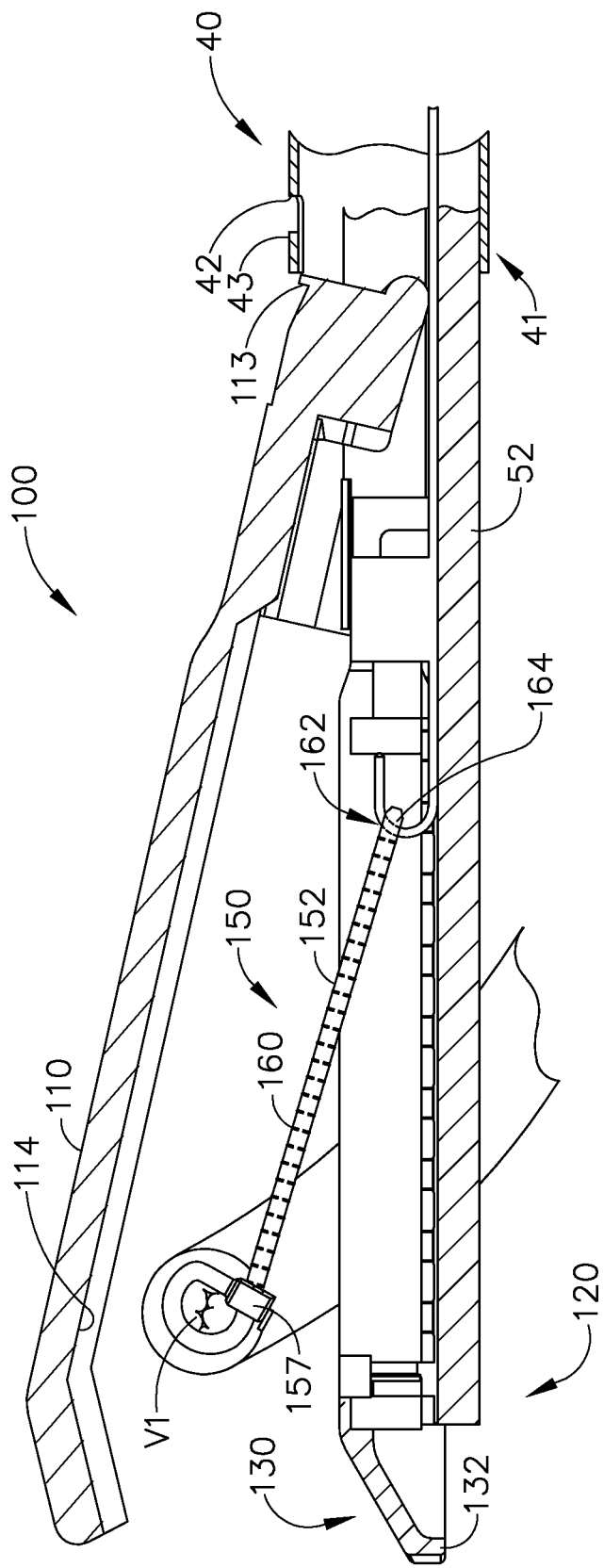
FIG. 11 is another cross-sectional view of the end effector depicted in FIG. 10 wherein the first jaw has been moved to an open position.
Figure 12:
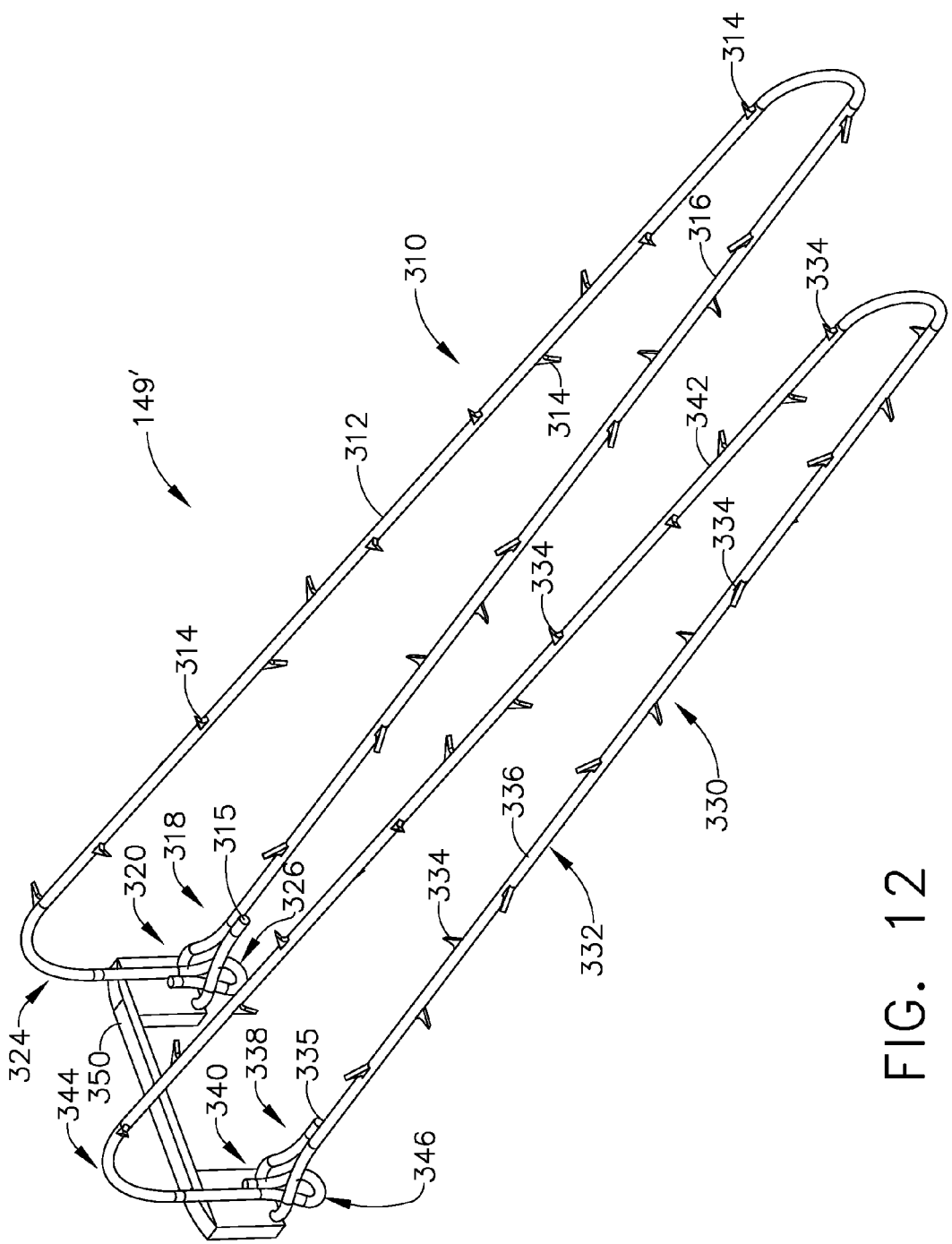
FIG. 12 is a perspective view of one form of another non-limiting closure assembly embodiment.

As can be seen in FIG. 9, the surgical instrument 10 further includes a closure retraction assembly 200. In various non-limiting embodiments, the closure retraction assembly 200 includes a first retraction hook 202 and a second retraction hook 204 that extend from a central actuation member 206. The retraction hooks 202, 204 may be fabricated from a suitable metal or other material and the central actuation member 206 may be fabricated from similar material. The central actuation member 206 extends through a longitudinal passage (not shown) in the spine 50 and interfaces with a retraction actuator 210 that is operably supported on the handle portion 30. The retraction actuator 210 may, for example, comprise a pivot member that is attached to or otherwise operably communicates with the central actuation member 206 such that by pivoting the retraction actuator 210 in the "A" direction (FIG. 1), the closure retraction assembly 200 will be pulled in the proximal direction "PD" (FIG. 9). As can be most particularly seen in FIG. 5, the first hook end 162 of the first suture strip 150 has a hook-receiving hole 164 therethrough that is adapted to be hookingly engaged by the first retraction hook 202 of the closure retraction assembly 200. Similarly, the second hook end 182 of the second suture strip 170 has a hook-receiving hole 184 therethrough that is adapted to be hookingly engaged by the second retraction hook 204 of the closure retraction assembly 200.

Operation of the surgical instrument 10 will now be described with reference to FIGS. 1, 3, 4 and 6-11. In use, the end effector 100 is introduced into the patient adjacent the vessel "V" to be cut and fastened. The end effector 100 may, for example, be introduced into the patient through a cannula of a trocar that has been installed in the patient. The end effector may also be inserted through an open incision in the patient as well. Once the end effector has been placed into the patient adjacent the vessel "V", jaw 110 is pivoted to the open position using the closure trigger 36 (FIG. 1). The clinician then manipulates the open end effector such that the vessel "V" is positioned between the jaws 110, 120 such that the vessel "V" is located between the upper suture portions 160, 180 and their corresponding lower suture portions 153, 173 supported on the cartridge deck face 140. See FIGS. 3 and 4.

Once the vessel "V" is received between the upper and lower suture portions 160, 180 as shown in FIGS. 3 and 4, the clinician can start to pivot the closure trigger 36 towards the pistol grip portion 34 of the handle portion 30 (FIG. 1) to advance the closure tube assembly 40 in the distal direction "DD". As the distal end 41 of the closure tube assembly 40 moves distally, it initially contacts the tab 113 on jaw 110. Continued movement of the closure tube assembly 40 in the distal direction "DD" moves jaw 110 distally relative to jaw 120 until the trunions 112 reach the top end of the trunion slots 54. Further distal movement of the closure tube assembly 40 causes the distal end 41 of the closure tube assembly 40 to slide distally over the tab 113 on jaw 110 such that the tab 113 is received within the horseshoe aperture 42 in the closure tube assembly 40. See FIG. 6. Such movement of the closure tube assembly 40 forces jaw 110 to pivot towards jaw 120. Such axial and pivotal travel of jaw 110 causes the suture hook ends 162, 182 to move into registration with the locking cavities 158, 177, respectively. Thereafter, the clinician pivots the retraction actuator 210 in the "A" direction (FIG. 1) to pull the closure retraction assembly 200 in the proximal direction "PD" (FIG. 9). Such movement of the closure retraction assembly 200 causes the first retraction hook 202 to hookingly engage the hook-receiving hole 164 of the first suture 150 and the second retraction hook 204 to hookingly engage the hook-receiving hole 184 of the second suture 170. Further pivotal travel of the retraction actuator 210 pulls the suture hook ends 162, 182 to cinch the sutures 150, 170 about the vessel "V" on opposite sides of the knife slot 134 in the cartridge body 132. The pointed locking tabs in each of the lock ends 157, 175 lock the sutures 150, 170 in position as was discussed above.

After the clinician has cinched the sutures 150, 170 about the vessel "V" on each side of the knife slot 134, the clinician then pivots the closure trigger 36 to the fully closed position wherein it is releasably locked using known locking structures. Such movement of the closure trigger 36 to the fully closed position causes jaw 110 to clamp the vessel "V" between the jaws 110, 120. Thereafter, the clinician advances the firing bar 16 distally by activating the firing trigger 38 or other actuator arrangement to thereby drive the tissue-cutting edge on the distal end 17 of the firing bar 16 through knife slot 134 in the cartridge body 132 an ultimately through the vessel "V". As the distal end 17 of the firing bar 16 is advanced distally through the end effector, the distal end may interact with the first jaw 110 to retain it in the clamped position as it cuts through the vessel. Such action cuts the vessel between the two cinched sutures 150, 170. The distal end of the firing bar 16 must then be withdrawn out of the end effector to enable the clinician to move jaw 110 to the open position and thereby release the cut vessel "V" therefrom.

After the vessel "V" has been cut to create a first occluded vessel end "V1" and a second occluded vessel end (not shown), the firing bar 16 is retracted. In various embodiments, for example, the firing trigger 28 springedly returns when the clinician removes pressure. Such action causes the retraction of the firing bar 16 in the proximal direction. Other firing bar retraction and retraction arrangements are known and may be employed. In the embodiment depicted in FIG. 1, a release button 31 interacts with the closure trigger such that when the release button is depressed, the closure trigger 36 is unlocked. The closure trigger 36 may be spring biased to return it to the starting position once it has been unlocked. Movement of the closure trigger 36 to the starting position causes the retraction of the closure tube assembly 40 in the proximal direction "PD". Such movement of the closure tube assembly 40 causes the tab 43 to contact the tab 113 on jaw 110 to move it to the initial starting or open position. See FIG. 11.

Once jaw 110 has been returned to the open position, the bridge 190 extending between the first and second sutures 150, 170 retains the first and second occluded vessel ends together to enable them to be inspected. Once the clinician has inspected the occluded vessel ends, the first and second sutures 150, 170 are cut to detach them from their respective closure retraction hooks 202, 204, respectively. If desired, the clinician may also cut the bridge 190 to separate the occluded ends of the vessel. Thereafter, the end effector 100 may be withdrawn from the patient. If the clinician wishes to reuse the device 10, the clinician must first remove the hook ends 156 and 176 from the previously used closure assembly 149 from their respective retraction hooks 202, 204 and return the retraction hooks 202, 204 to their respective starting positions in the cartridge body 132 (FIG. 4). A closure assembly 149 is then installed into the cartridge body 132 (FIG. 3). Thereafter, the instrument 10 may again be reused.

FIGS. 12-18 illustrate the use of the device 10 in connection with another form of a flexible elongated tissue closure assembly 149'. As can be most particularly seen in FIG. 12, the closure assembly 149' comprises a first absorbable closure member 310 that has a body portion 312 that has a plurality of unidirectional barbs 314 formed thereon. The closure assembly 149' further includes a second absorbable closure member 330 that has a body portion 332 that has a plurality of unidirectional barbs 334 formed thereon. The first and second closure members 310, 330 may be fabricated from those wound closure devices manufactured by Covidien of Mansfield, Mass. under the trademark V-Loc™. As can be further seen in FIG. 12, the body portion 312 of the first closure member 310 has a first elongated lower portion 316 that terminates in a first lock end 318 wherein the end 315 is looped around and welded to form a first locking loop 320. The first closure member 310 further has a first elongated upper portion 322 that is integrally formed with the first elongated lower portion 316 and has a first hook-shaped end 324. The first hook-shaped end 324 terminates in a welded first distal loop 326 that extends through the first locking loop 320. Similarly, the body portion 332 of the second closure member 330 has a second elongated lower portion 336 that terminates in a second lock end 338 wherein the end 335 is looped around and welded to form a second locking loop 340. The second closure member 330 further has a second elongated upper portion 342 that is integrally formed with the second elongated lower portion 336 and has a second hook-shaped end 344. The second hook-shaped end 344 terminates in a welded second distal loop 346 that extends through the second locking loop 340. In various embodiments, the locking loops 320, 340 are attached to an absorbable bridge 350.

The flexible elongated tissue closure assembly 149' may be installed into the cartridge body 132 in the manner described above with respect to the closure assembly 149. In this embodiment, however, jaw 110' which is otherwise substantially identical to jaw 110 described above has two downwardly projecting lateral fins 115 to provide further support to the first and second closure members 310, 330. See FIGS. 13 and 14.

Figure 13:
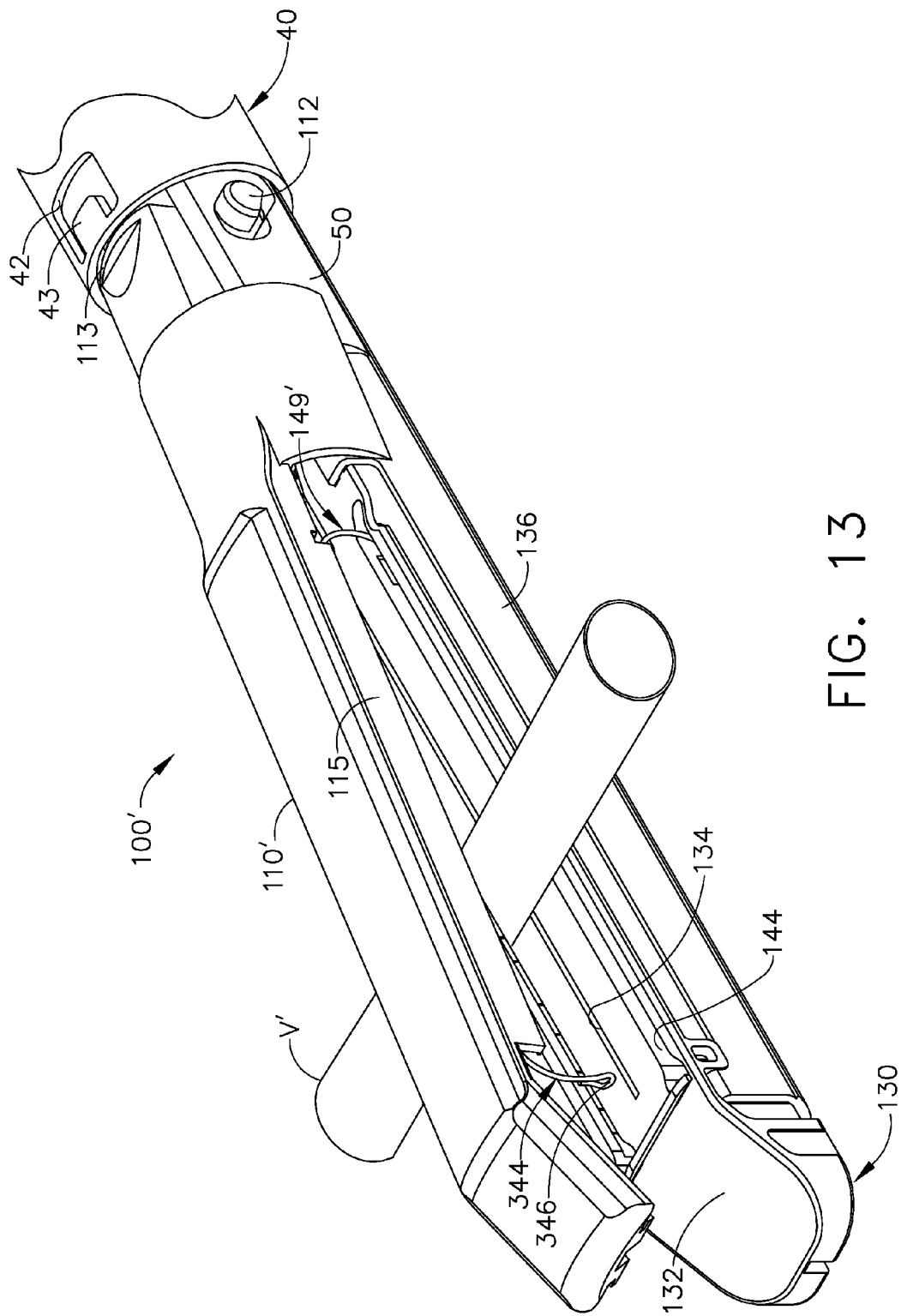
FIG. 13 is a perspective view one form of a non-limiting end effector embodiment operably supporting a wound closure assembly embodiment and a portion of a vessel therein.
Figure 14:
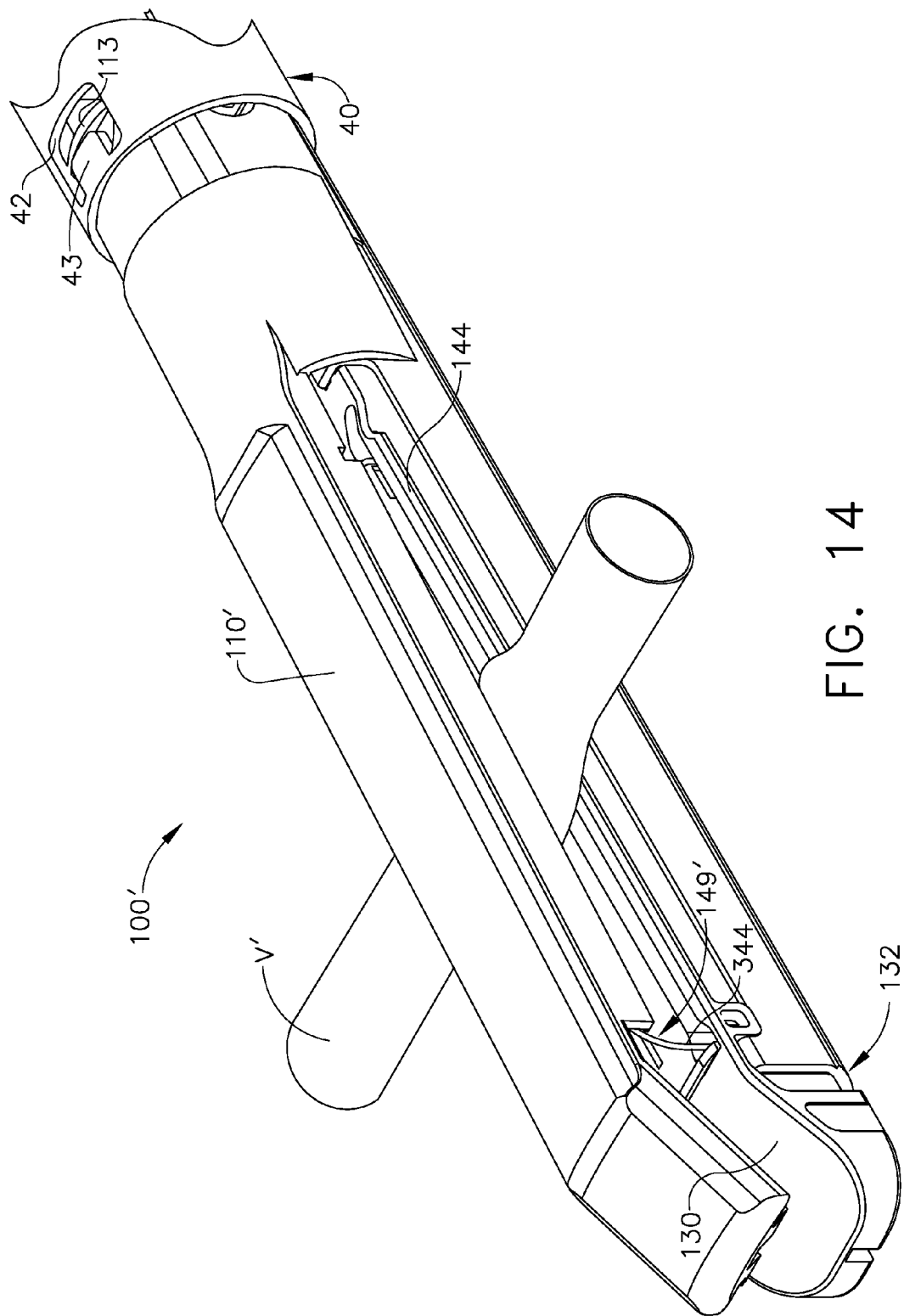
FIG. 14 is a perspective view the end effector of FIG. 13 in a clamped orientation.
Figure 15:
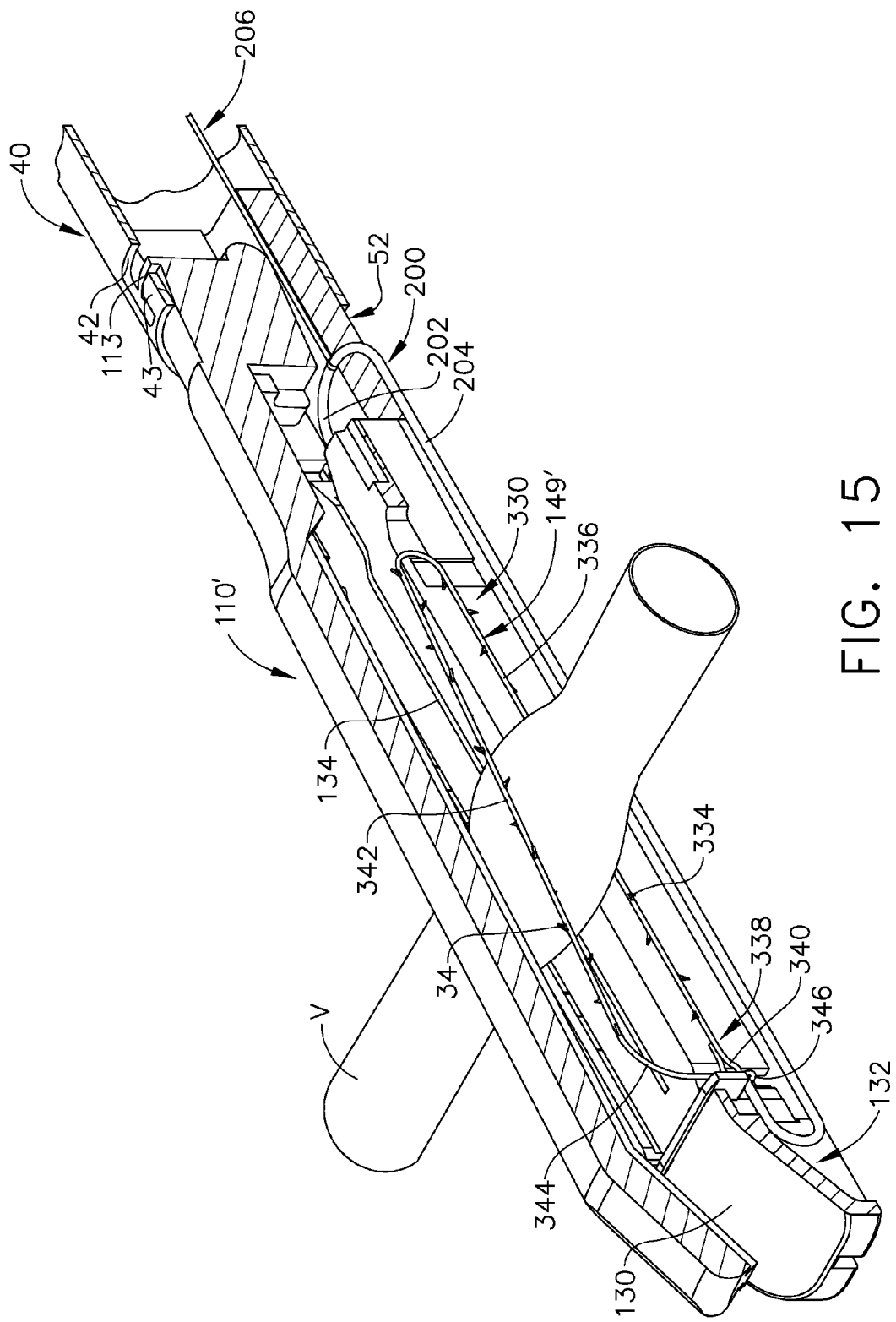
FIG. 15 is a cross-sectional perspective view of the end effector of FIG. 14.
Figure 16:
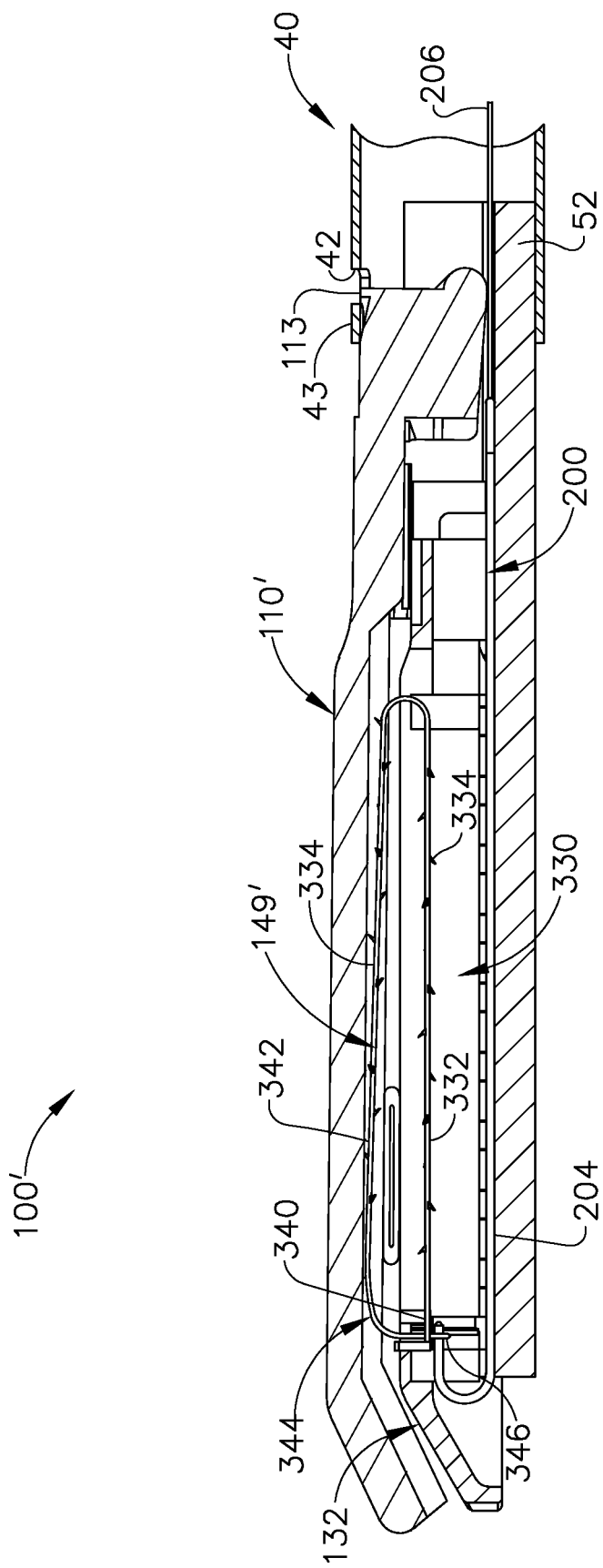
FIG. 16 is another cross-sectional view of the end effector of FIGS. 14 and 15.
Figure 17:
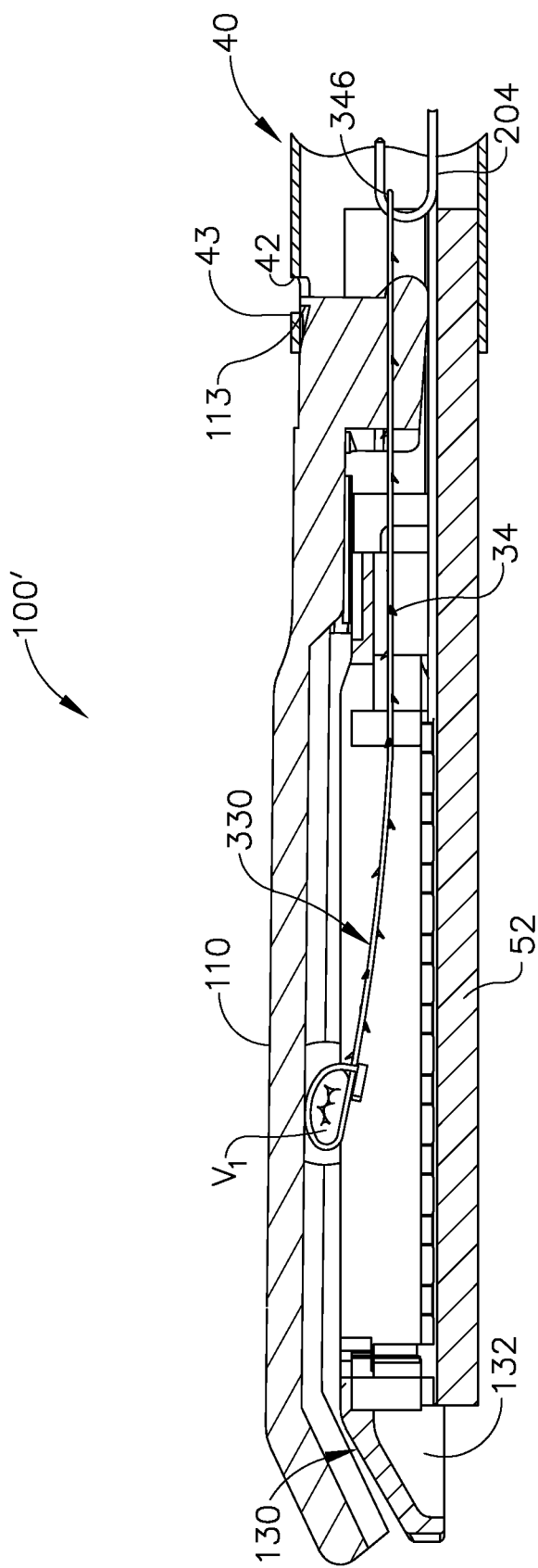
FIG. 17 is another cross-sectional view of the end effector of FIGS. 14-16 after the wound closure devices have been retracted and the firing bar has cut through the vessel.
Figure 18:
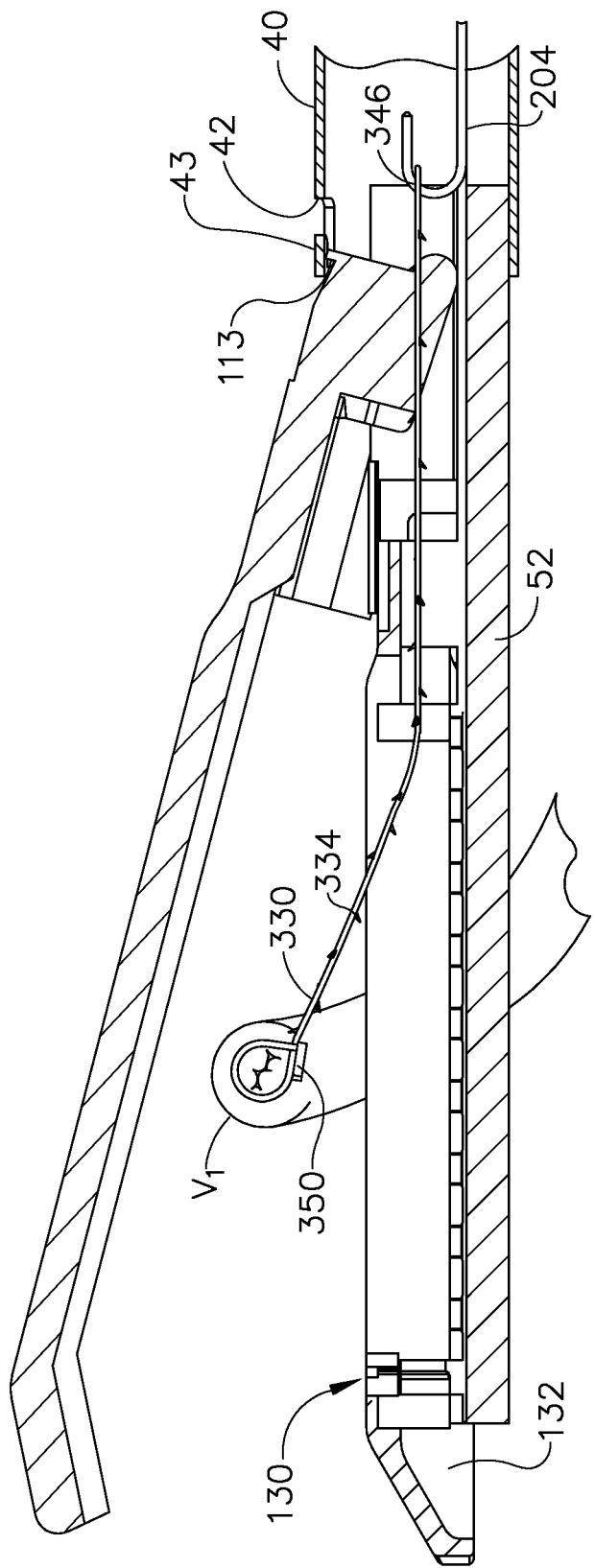
FIG. 18 is another cross-sectional view of the end effector depicted in FIG. 17 wherein the first jaw has been moved to an open position.

Operation of the instrument 10 with the flexible elongated tissue closure assembly 149' can be understood with reference to FIGS. 13-18. FIG. 13 depicts the end effector 100 after it has been introduced into the patient and the vessel "V" has been acquired between the jaws 110' and 120. The clinician then starts to pivot the closure trigger 36 towards the pistol grip portion 34 of the handle 30 (FIG. 1) to advance the closure tube assembly 40 in the distal direction "DD". As the distal end 41 of the closure tube assembly 40 moves distally, it initially contacts the tab 113 on jaw 110'. Continued movement of the closure tube assembly 40 in the distal direction "DD" moves jaw 110' distally relative to jaw 120 until the trunions 112 reach the top end of the trunion slots 54. Further distal movement of the closure tube assembly 40 causes the distal end 41 of the closure tube assembly 40 to slide distally over the tab 113 on jaw 110' such that the tab 113 is received within the horseshoe aperture 42 in the closure tube assembly 40. See FIG. 14. Such movement of the closure tube assembly 40 forces jaw 110' to pivot towards jaw 120. Such axial and pivotal travel of jaw 110' causes the hooked portions 320, 340 and more particularly the distal loops 322, 342 to move into registration with the respective locking loops 318, 328. Thereafter, the clinician pivots the retraction actuator 210 in the "A" direction (FIG. 1) to pull the closure retraction assembly 200 in the proximal direction "PD" (FIG. 15). Such movement of the closure retraction assembly 200 causes the first retraction hook 202 to hookingly engage the distal loop 322 of the first closure member 310 and the second retraction hook 204 to hookingly engage the second distal loop 342 of the second closure member 330. Further pivotal travel of the retraction actuator 210 pulls the hook ends 202, 204 to cinch the closure members 310, 330 about the vessel "V" on opposite sides of the knife slot 134 in the cartridge body 132.

After the clinician has cinched the wound closure members 310, 330 about the vessel "V" on each side of the knife slot 134, the clinician then pivots the closure trigger 36 to the fully closed position wherein it is releasably locked using known locking structures. Such movement of the closure trigger 36 to the fully closed position causes jaw 110' to clamp the vessel "V" between jaws 110', 120. See FIG. 16. Thereafter, the clinician advances the firing bar 16 distally by activating the firing trigger 38 or other actuator arrangement to thereby drive the tissue-cutting edge on the distal end of the firing bar 16 through knife slot 134 in the cartridge body 132 an ultimately through the vessel "V".

After the vessel "V" has been cut to create a first occluded vessel end "V1" and a second occluded vessel end (not shown), the firing bar 16 is retracted. The clinician may then move jaw 110' to the open position shown in FIG. 18. The bridge 150 extending between the first and second closure members 310, 330 retains the first and second occluded vessel ends together for inspection. Once the clinician has inspected the occluded ends, the first and second closure members 310, 330 are cut to detach them from their respective retraction hooks 202, 204, respectively. If desired, the clinician may also cut the bridge 350 to separate the occluded ends of the vessel. Thereafter, the end effector 100 may be withdrawn from the patient. If the clinician wishes to reuse the device 10, the clinician must first remove the looped ends 322, 342 from their respective retraction hooks 202, 204 and return the retraction hooks 202, 204 to their respective starting positions in the cartridge body 132 (FIG. 15). A new closure assembly 149' is then installed into the cartridge body 132. Thereafter, the instrument 10 may again be reused.

Figure 19:
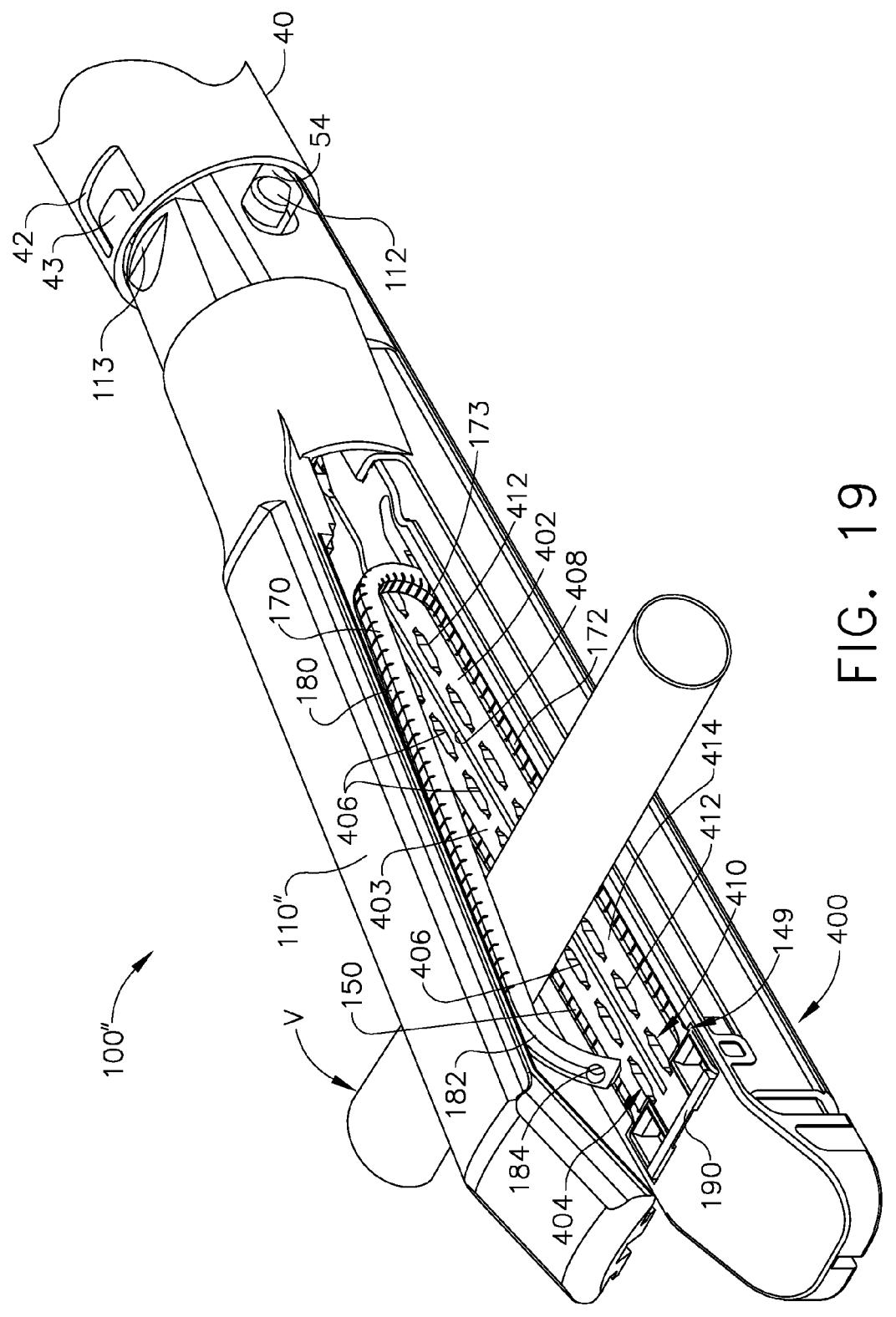

FIG. 19 illustrates another end effector embodiment 100" that may be used in connection with the instrument 10. This non-limiting embodiment employs a fastener cartridge 400 that is configured to also deploy a single line of surgical staples on each side of the vessel cut line. A variety of surgical staple cartridge arrangements are known. For example, U.S. Pat. No. 7,000,818 which has been herein incorporated by reference, discloses various forms of surgical staple cartridges. The cartridge 400 of various embodiments of the present invention may be substantially similar to those cartridges or other known staple cartridges except for the differences noted below. For example, in addition to a first row 404 of staple openings 406 located in the cartridge body 402 on the first side 403 of the elongated knife slot 408 and a second row of 410 of staple openings 412 on the second side 414 of the elongated knife slot 408, the cartridge body 402 is also configured as described above to operably support one of the closure assemblies 149, 149' in the manners described above.

Jaw 110" of the end effector 100" is substantially similar to the jaws 110, 110' as described above, except that the jaw 110" also is configured to act as an anvil for forming the staples supported within the cartridge 400. For example, the undersurface of jaw 110" is provided with two series of staple forming pockets that register with the corresponding staple openings in the cartridge body 402 when the jaw 110" is pivoted and locked into the clamping position. Such staple forming pockets serve to form the staples as they driven through the vessel "V" in a known manner.

The end effector 100" may also be used/activated in a similar manner as was described above with respect to the end effectors 100, 100'. For example, the clinician manipulates jaw 110" in the above described manners to acquire the vessel "V" as shown in FIG. 19. Jaw 110" is then locked into clamping position and the clinician may then actuate the retraction actuator 210 to cinch the sutures or closure members which ever the case may be. When the clinician then actuates the firing bar 16 to move distally, the firing bar 16 will not only cut the through the vessel, the firing bar also causes the staples that are operably supported in the staple pockets to be driven out of the staple pockets into the corresponding staple forming pockets provided in the underside of jaw 110". For example, as described in U.S. Pat. No. 7,000,818, the staples may be operably supported on staple driver members that are movably supported in each of the staple pockets in the cartridge body. As the distal end portion of the firing bar 16 is driven distally into the cartridge body 402, it interacts with a wedge sled movably supported therein. As the wedge sled is distally advanced through the cartridge body 402 by the firing bar 16, the staple drivers are forced upward within their respective pockets to thereby drive out the staples support thereon out of the pocket and into forming contact with the underside of jaw 110" and ultimately through the cut ends of the vessel. Thus, the occluded ends of the vessel are not only sealed with a suture or wound closure device, they are also sealed with a line of staples.

The non-limiting embodiments described herein have been described in the context of surgical instrument arrangements that are handheld and manually operated or actuated. Those of ordinary skill in the art will readily understand that the unique and novel features of the various non-limiting embodiments of the present invention disclosed may also be effectively attained in applications wherein the closure devices used to open and close the jaws as well as those control arrangements for activating the firing bar and suture actuation members may be controlled by a robot or robots or by other automated system arrangements. Accordingly, the protection afforded to the various non-limiting embodiments disclosed herein should not be limited to instruments that are handheld and/or are manually operated. Further, the various non-limiting embodiments disclosed herein may be affectively employed with surgical instrument arrangements that are powered (e.g., by electricity, pneumatics, fluids, etc.) and that may or may not be handheld and that may or may not be manually actuated or actuated by robots or other automated control system arrangements. The various embodiments of the present invention disclosed herein are intended to encompass such modifications.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical fastening instrument, comprising:
   a first jaw operably supporting a substantially flexible elongated tissue closure assembly therein comprising a first suture strip including a first end and a second end, wherein the first suture strip comprises an aperture in the first end, and wherein the second end is configured to be pulled through the aperture in the first end;
   a second jaw movably supported relative to the first jaw and being selectively movable between open and closed positions in response to opening and closing motions applied thereto; and
   a closure retraction assembly configured to selectively pull the second end of the first suture strip through the aperture in the first end of the first suture strip to cinch the first suture strip around tissue received between the first and second jaws.

2. The surgical fastening instrument of claim 1 wherein the substantially flexible elongated tissue closure assembly further comprises:
   a second suture strip including another first end and another second end, wherein the second suture strip comprises another aperture, and wherein the another second end is configured to be pulled through the another aperture in the another first end by the closure retraction assembly.

3. The surgical fastening instrument of claim 2 wherein said first and second suture strips are linked together by a bridge member.

4. The surgical fastening instrument of claim 2 wherein said first suture strip comprises:
   a first substantially U-shaped flexible first body portion terminating in said first end and said second end such that said aperture comprises a locking aperture and said second end comprises a hook-shaped end spaced from said locking aperture and in substantial registration therewith and wherein said second suture strip comprises a second substantially U-shaped flexible second body portion terminating in said another second end such that said another aperture comprises another locking aperture and said another second end comprises another hook-shaped end spaced from said another locking aperture and in substantial registration therewith.

5. The surgical fastening instrument of claim 4 wherein said closure retraction assembly comprises:
a first retraction hook that is movably supported for selective hooking engagement with said hook-shaped end after said hook-shaped end has been advanced through said locking aperture; and
a second retraction hook that is movably supported for selective hooking engagement with said another hook-shaped end after said another hook-shaped end has been advanced through said another locking aperture.

6. The surgical fastening instrument of claim 1 wherein said first suture strip comprises a first absorbable closure member having a plurality of unidirectional barbs thereon.

7. The surgical fastening instrument of claim 6 wherein said first absorbable closure member comprises a first substantially U-shaped flexible first body portion terminating in a first locking end that defines a first locking aperture and a first hook-shaped end spaced from said first locking aperture and in substantial registration therewith.

8. The surgical fastening instrument of claim 1 further comprising:
a first plurality of staples operably supported in said first jaw on a first side of a slot configured to receive a cutting member therein; and
a second plurality of staples operably supported in said first jaw on a second side of said slot.

9. The surgical fastening instrument of claim 2 wherein said first suture strip comprises a first absorbable closure member having a plurality of unidirectional barbs thereon and wherein said second suture strip comprises a second absorbable closure member having a plurality of unidirectional barbs thereon.

10. The surgical fastening instrument of claim 9 wherein said first and second absorbable closure members are linked together by an absorbable bridge member.

11. The surgical fastening instrument of claim 9 wherein said first absorbable closure member comprises a first substantially U-shaped flexible first body portion terminating in a first locking end that defines a first locking aperture and a first hook-shaped end spaced from said first locking aperture and in substantial registration therewith and wherein said second absorbable closure member comprises a second substantially U-shaped flexible second body portion terminating in a second locking end that defines a second locking aperture and a second hook-shaped end spaced from said second locking aperture and in substantial registration therewith.

12. The surgical fastening instrument of claim 11 wherein said first locking end and said second locking end are linked together by a bridge member.

13. The surgical fastening instrument of claim 2 wherein the first and second suture strips are bioabsorbable.

14. The surgical fastening instrument of claim 3 wherein the first and second suture strips and the bridge member are bioabsorbable.

15. The surgical fastening instrument of claim 2 further comprising:
a first plurality of staples operably supported in said first jaw on a first side of a slot configured to receive a cutting member therein; and
a second plurality of staples operably supported in said first jaw on a second side of said slot.

16. A surgical fastening instrument, comprising:
a first jaw operably supporting a substantially flexible elongated tissue closure assembly therein, said substantially flexible elongated tissue closure assembly comprising:
a first absorbable suture comprising a first substantially U-shaped flexible first body portion terminating in a first locking end that defines a first locking aperture and a first hook-shaped end spaced from said first locking aperture and in substantial registration therewith; and
a second absorbable suture comprising a second substantially U-shaped flexible second body portion terminating in a second locking end that defines a second locking aperture and a second hook-shaped end spaced from said second locking aperture and in substantial registration therewith, and wherein said surgical fastening instrument further comprises:
a second jaw movably supported relative to said first jaw and being selectively movable between open and closed positions in response to opening and closing motions applied thereto; and
a closure retraction assembly configured to selectively apply cinching motions to said substantially flexible elongated tissue closure assembly.

17. The surgical fastening instrument of claim 16 wherein said first and second absorbable sutures are linked together by an absorbable bridge member.

18. The surgical fastening instrument of claim 16 wherein said closure retraction assembly comprises:
a first retraction hook that is movably supported for selective hooking engagement with said first hook-shaped end after said first hook-shaped end has been advanced through said first locking aperture; and
a second retraction hook that is movably supported for selective hooking engagement with said second hook-shaped end after said second hook-shaped end has been advanced through said second locking aperture.

19. The surgical instrument of claim 16 wherein said first absorbable suture and said second absorbable suture each include a plurality of unidirectional barbs.

20. The surgical fastening instrument of claim 19 wherein said first and second absorbable closure members are linked together by an absorbable bridge member.

21. The surgical fastening instrument of claim 16 further comprising:
a first plurality of staples operably supported in said first jaw on a first side of a slot configured to receive a cutting member therein; and
a second plurality of staples operably supported in said first jaw on a second side of said slot.

22. A surgical fastening instrument, comprising:
a first jaw operably supporting a tissue securing assembly therein comprising a first strip including a first end and a second end, wherein the first strip comprises an aperture in the first end, and wherein the second end is configured to be pulled through the aperture in the first end;
a second jaw, wherein one of the first jaw and the second jaw is movable between an open position and a closed position; and
a closure assembly configured to selectively pull the second end through the aperture in the first end to cinch the tissue securing assembly around tissue received between the first and second jaws.

23. A surgical fastening instrument, comprising:
a first jaw operably supporting a tissue securing assembly therein, the tissue securing assembly comprising:
a first suture comprising a first flexible body portion terminating in a first locking end that defines a first locking aperture and a first hook-shaped end spaced from the first locking aperture; and a second suture comprising a second flexible body portion terminating in a second locking end that defines a second locking aperture and a second hook-shaped end spaced from the second locking aperture;
a second jaw, wherein one of the first jaw and the second jaw is movable between an open position and a closed position; and
a closure retraction assembly configured to selectively apply a cinching motion to the tissue securing assembly.

* * * * *